(12) United States Patent
Yoshida et al.

(10) Patent No.: US 9,977,037 B2
(45) Date of Patent: May 22, 2018

(54) CAPILLARY NETWORK DEVICES AND METHODS OF USE

(71) Applicants: New Health Sciences, Inc., Bethesda, MD (US); The Administrators of the Tulane Educational Fund, New Orleans, LA (US)

(72) Inventors: Tatsuro Yoshida, West Newton, MA (US); Sergey S. Shevkoplyas, Friendswood, TX (US); Jennie M. Burns, New Orleans, LA (US)

(73) Assignees: New Health Sciences, Inc., Lexington, MA (US); The Administrators of the Tulane Educational Fund, New Orleans, LA (US)

( * ) Notice: Subject to any disclaimer, the term of this patent is extended or adjusted under 35 U.S.C. 154(b) by 0 days. days.

(21) Appl. No.: 14/403,365

(22) PCT Filed: May 22, 2013

(86) PCT No.: PCT/US2013/042314
§ 371 (c)(1),
(2) Date: Nov. 24, 2014

(87) PCT Pub. No.: WO2013/177339
PCT Pub. Date: Nov. 28, 2013

(65) Prior Publication Data
US 2015/0153367 A1 Jun. 4, 2015

Related U.S. Application Data

(60) Provisional application No. 61/650,283, filed on May 22, 2012.

(51) Int. Cl.
*G01N 33/80* (2006.01)
*B01L 3/00* (2006.01)

(52) U.S. Cl.
CPC ............ *G01N 33/80* (2013.01); *B01L 3/5027* (2013.01); *B01L 3/502715* (2013.01);
(Continued)

(58) Field of Classification Search
CPC .. G01N 33/80; B01L 3/5027; B01L 3/502715
(Continued)

(56) References Cited

U.S. PATENT DOCUMENTS 5,023,054 A 6/1991 Sato et al.
5,427,663 A 6/1995 Austin et al.
(Continued)

FOREIGN PATENT DOCUMENTS

WO WO 96/39026 A1 12/1996
WO WO 04/078029 A2 9/2004
(Continued)

OTHER PUBLICATIONS

Mak, M. et al. (2011). "Microfabricated Physical Spatial Gradients for Investigating Cell Migration and Invasion Dynamics." 6(6):e20825.*
(Continued)

*Primary Examiner* — Jill A Warden
*Assistant Examiner* — Jacqueline Brazin
(74) *Attorney, Agent, or Firm* — Arnold & Porter Kaye Scholer LLP

(57) ABSTRACT

Artificial microvascular network (AMVN) devices are provided and related methods of making and methods of using such devices are provided. The present disclosure generally relates to an AMVN device comprising a substrate including a capillary network configured so as to simulate those actually encountered in the circulation of various humans and animal model systems. In certain aspects, the AMVN devices may be used, e.g., to investigate the effect of storing
(Continued)

RBCs under aerobic and anaerobic conditions. However, the use of such AMVN devices is not so limited.

30 Claims, 29 Drawing Sheets

(52) U.S. Cl.
CPC .................. *B01L 2300/0838* (2013.01); *B01L 2300/0861* (2013.01); *B01L 2300/0867* (2013.01)

(58) Field of Classification Search
USPC ........................................................ 422/502
See application file for complete search history.

(56) References Cited

U.S. PATENT DOCUMENTS

| | | | |
|---|---|---|---|
| 5,506,141 | A | 4/1996 | Weinreb et al. |
| 5,635,358 | A | 6/1997 | Wilding et al. |
| 5,972,710 | A | 10/1999 | Weigl et al. |
| 6,027,623 | A | 2/2000 | Ohkawa |
| 6,148,536 | A | 11/2000 | Iijima |
| 6,368,871 | B1 | 4/2002 | Christel et al. |
| 6,465,257 | B1* | 10/2002 | Parce .................. B01L 3/50273 204/450 |
| 7,208,120 | B2 | 4/2007 | Bitensky et al. |
| 7,517,453 | B2 | 4/2009 | Bitensky et al. |
| 2002/0086329 | A1 | 7/2002 | Shvets et al. |
| 2002/0176798 | A1 | 11/2002 | Linker et al. |
| 2002/0182241 | A1 | 12/2002 | Borenstein et al. |
| 2003/0003575 | A1 | 1/2003 | Vacanti et al. |
| 2004/0013566 | A1 | 1/2004 | Myrick et al. |
| 2004/0168982 | A1 | 9/2004 | Bitensky et al. |
| 2006/0118479 | A1* | 6/2006 | Shevkoplyas ..... B01L 3/502761 210/433.1 |
| 2008/0027368 | A1 | 1/2008 | Kollar et al. |
| 2009/0269837 | A1* | 10/2009 | Shevkoplyas ......... B01L 3/5027 435/287.1 |
| 2010/0112723 | A1* | 5/2010 | Battrell ............. B01L 3/502776 436/501 |

FOREIGN PATENT DOCUMENTS

| | | |
|---|---|---|
| WO | WO 2009/039378 A2 | 3/2009 |
| WO | WO 2013/177339 A1 | 11/2013 |

OTHER PUBLICATIONS

Anderson et al., "Microfabrication and microfluidics for tissue engineering: state of the art and future opportunities," *Lab Chip*, 4:98-103 (2004).
Borenstein et al., "Microfabrication Technology for Vascularized Tissue Engineering," *Biomedical Microdevices*, 4(3):167-175 (2002).
Brody et al., "Deformation and Flow of Red Blood Cells in a Synthetic Lattice: Evidence for an Active Cytoskeleton," *Biophysical Journal*, 68:2224-2232 (1995).
Burns et al., "Artificial microvascular network: a new tool for measuring rheologic properties of stored red blood cells," *Transfusion*, 52(5):1010-1023 (2012).
Carr et al., "Nonlinear Dynamics of Microvascular Blood Flow," *Annals of Biomedical Engineering*, 28:641-652 (2000).
Cell Deformability, RheoSCAN (RheoScan-AnD300/RheoScan-D300), obtained on Dec. 11, 2012, from: http://www.rheoscan.com/products/products/products-01.html.
Cokelet et al., "Fabrication of in Vitro Microvascular Blood Flow Systems by Photolithography," *Microvascular Research*, 46:394-400 (1993).
De Angelis et al., "Erythrocyte Shape Control in Stored Blood: The Effect of Additive Solutions on Shape Recovery," *Haematologica*, 73:7-12 (1988).

Dumont et al., "Performance of Anaerobic Stored Red Blood Cells Prepared Using a Prototype $O_2$ & $CO_2$ Depletion and Storage System," *Transfusion*, 51(suppl):77A (2011).
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
Fahraeus et al., "The Viscosity of the Blood in Narrow Capillary Tubes," *Am. J. Physiol.*, 96(3):562-568 (1931).
Forouzan et al., "Passive recruitment of circulating leukocytes into capillary sprouts from existing capillaries in a microfluidic system," *Lab Chip*, 11:1924-1932 (2011).
Frame et al., "A System for Culture of Endothelial Cells in 20-50-μ Branching Tubes," *Microcirculation*, 2(4):377-385 (1995).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Gifford et al., "A detailed study of time-dependent changes in human red blood cells: from reticulocyte maturation to erythrocyte senescence," *British Journal of Haematology*, 135:395-404 (2006).
Gifford et al., "Parallel Microchannel-Based Measurements of Individual Erythrocyte Areas and Volumes," *Biophysical Journal*, 84:623-633 (2003).
Griffith, "Temporal chaos in the microcirculation," *Cardiovascular Research*, 31:342-358 (1996).
Hulme et al., "Lifespan-on-a-chip: microfluidic chambers for performing lifelong observation of *C. elegans*," *Lab Chip*, 10:589-597 (2010).
International Search Report dated Aug. 13, 2013, in International Patent Application No. PCT/US2013/042314.
Jain, et al., "Determinants of Leukocyte Margination in Rectangular Microchannels," *PLoS ONE*, 4(9):1-8 (2009).
Jayasinghe et al., "Controlled deposition of nanoparticle clusters by electrohydrodynamic atomization," *Nanotechnology*, 15:1519-1523 (2004).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Johnson et al., "Regulation of blood flow in single capillaries," *American Journal of Physiology*, 212:1405-1415 (1967).
Kaihara et al., "Silicon Micromachining to Tissue Engineer Branched Vascular Channels for Liver Fabrication," *Tissue Engineering*, 6(2):105-117 (2000).
Kiani et al., "Fluctuations in microvascular blood flow parameters caused by hemodynamic mechanisms," *American Journal of Physiology*, 266(5):H1822-H1828 (1994).
Kikuchi et al., "Modified Cell-Flow Microchannels in a Single-Crystal Silicon Substrate and Flow Behavior of Blood Cells," *Microvascular Research*, 47:126-139 (1994).
Krogh, "Studies on the physiology of capillaries. II. The reactions to local stimuli of the blood-vessels in the skin and web of the frog," *The Journal of Physiology*, 55:412-422 (1921).
McDonald et al., "Poly(dimethylsiloxane) as a Material for Fabricating Microfluidic Devices," *Accounts of Chemical Research*, 35(7):491-499 (2002).
Moroff et al., "Proposed standardization of methods for determining the 24-hour survival of stored red cells," *Transfusion*, 24:109-114 (1984).
Ng et al., "Components for integrated poly(dimethylsiloxane) microfluidic systems," *Electrophoresis*, 23:3461-3473 (2002).
Pries et al., "Biophysical aspects of blood flow in the microvasculature," *Cardiovascular Research*, 32:654-667 (1996).
Sambuceti et al., "Why should we study the coronary microcirculation?," *Am J Physiol Heart Circ Physiol*, 279:H2581-H2584 (2000).
Shevkoplyas et al., "Prototype of an in vitro model of the microcirculation," *Microvasc Res*, 65(2):132-136 (2003).
Shevkoplyas et al., "Direct measurement of the impact of impaired erythrocyte deformability on microvascular network perfusion in a microfluidic device," *Lab Chip*, 6:914-920 (2006).

(56) References Cited

OTHER PUBLICATIONS

Shin et al., "A transient, microfluidic approach to the investigation of erythrocyte aggregation: the threshold shear-stress for erythrocyte disaggregation," *Clin Hemorheol Microcirc*, 42:117-125 (2009).
Sia et al., "Microfluidic devices fabricated in poly(dimethylsiloxane) for biological studies," *Electrophoresis*, 24:3563-3576 (2003).
Skalak et al., "Deformation of Red Blood Cell in Capillaries," *Science*, 164(3880):717-719 (1969).
Sutton et al., "A Novel Instrument for Studying the Flow Behavior of Erythrocytes through Microchannels Simulating Human Blood Capillaries," *Microvascular Research*, 53:272-281 (1997).
The International Committee for Standardization in Hematology, "Recommended Methods for Radioisotope Red Cell Survival Studies," *Blood*, 38(3):378-386 (1971).
Tracey et al., "A Silicon Micromachined Device for Use in Blood Cell Deformability Studies," *IEEE Transactions on Biomedical Engineering*, 42(8):751-761 (1995).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Wang et al., "Fabrication of PLGA microvessel scaffolds with circular microchannels using soft lithography," *Journal of Micromechanics and Microengineering*, 17(10):2000-2005 (2007).
Wilding et al., "Manipulation and Flow of Biological Fluids in Straight Channels Micromachined in Silicon," *Clinical Chemistry*, 40(1):43-47 (1994).
Wu et al., "Polymer microchips bonded by $O_2$-plasma activation," *Electrophoresis*, 23:782-790 (2002).
Xia et al., "Soft Lithography," *Angew. Chem. Int.*, 37:550-575 (1998).
Zhang et al., "Modification of Si(100) surface by the grafting of poly(ethylene glycol) for reduction in protein adsorption and platelet adhesion," *J Biomed Mater Res*, 56:324-332 (2001).
Gifford et al., "A high-resolution, double-labeling method for the study of in vivo red blood cell aging," *Transfusion* 46:578-588 (2006).
Barbee et al., "The Fahraeus Effect," Microvascular Research, 3:6-16 (1971).
Barclay et al., "A Method for Detecting Chaos in Canine Myocardial Microcirculatory Red Cell Flux," Microcirculation, Nature America Inc. 7:335-346 (2000).
Barras et al., "Influence of Rejuvenation on the Rheological Properties of Stored Erythrocytes," VASA, 23(4):305-311 (1994).
Countess Cell Counting Chamber Slides for Countess Automated Cell Counter—Box of 50, Invitrogen Corporation, The Handbook (1):15.3 Viability and Cytotoxicity Assay Kits for Diverse Cell Types (2008).
Dumont et al., "Anaerobic storage of red blood cells in a novel additive solution improves in vivo recovery," Transfusion, 49(3):458-464 (2009).
European Office Action dated Apr. 13, 2017 in European Appln. No. 10 765 101.0.
European Search Report dated Feb. 11, 2005, in European Patent Application No. 02 78 2307.9.
Extended European Search Report, dated Aug. 8, 2014 for European Patent Application No. 10823965.8.
Extended European Search Report, dated Oct. 23, 2014, for European Patent Application No. 11838889.1.
Extended European Search Report dated Nov. 4, 2014, in European Patent Application No. 12807324.4.
Extended European Search Report dated Mar. 5, 2015, in European Patent Application No. 12821624.9.
Greenwalt et al., "The effect of hypotonicity, glutamine, and glycine on red cell preservation," Transfusion, 37:269-276 (1997).
Högman et al., "Cell Shape and Total Adenylate Concentration as Important Factors for Posttransfusion Survival of Erythrocytes," Biomed. Biochim. Acta, 42:S327-S331 (1983).
Huang et al., "Continuous Particle Separation Through Deterministic Lateral Displacement," Science, 304:987-990 (2004).
International Search Report completed on Jul. 8, 1996, in International Patent Application No. PCT/US96/09005.
International Search Report completed on Nov. 10, 2003, in International Patent Application No. PCT/US02/36735.
International Search Report dated Dec. 2005, in International Patent Application No. PCT/US2004/006040.
International Search Report dated Aug. 4, 2010, in International Patent Application No. PCT/US2010/031055.
International Search Report dated Nov. 22, 2010, in International Patent Application No. PCT/US2010/052376.
International Search Report dated Apr. 26, 2011, in International Patent Application No. PCT/US2010/044045.
International Search Report dated Dec. 21, 2011, in International Patent Application No. PCT/US11/49168.
International Search Report completed on Feb. 12, 2012, in International Patent Application No. PCT/US11/59372.
International Preliminary Report on Patentability completed on Feb. 14, 2012, in International Patent Application No. PCT/US2010/52084.
International Preliminary Report on Patentability completed on May 21, 2012, in International Patent Application No. PCT/US2010/52376.
International Search Report completed on Jun. 18, 2012, in International Patent Application No. PCT/US12/30930.
International Search Report completed on Sep. 24, 2012, in International Patent Application No. PCT/US12/50380.
International Search Report completed on Nov. 9, 2012, in International Patent Application No. PCT/US12/45426.
International Search Report completed on Jul. 10, 2014, in International Patent Application No. PCT/US2014/019537.
Moll et al., "Dean vortices applied to membrane process. Part II: Numerical approach," Journal of Membrane Science, 288:321-335 (2007).
Supplementary European Search Report dated Jan. 20, 2015 in European Patent Application No. 12822378.2.

\* cited by examiner

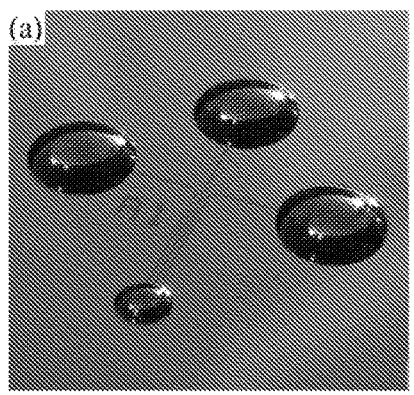 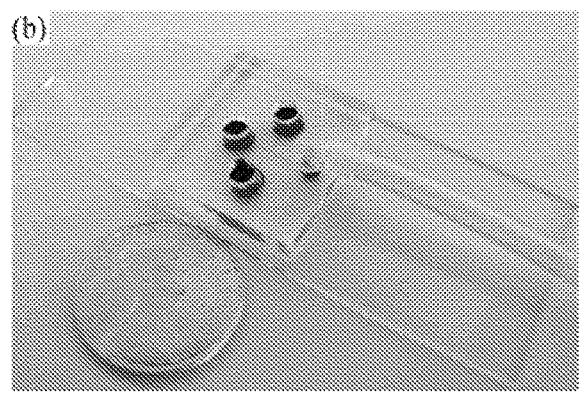
FIG. 2A    FIG. 2B
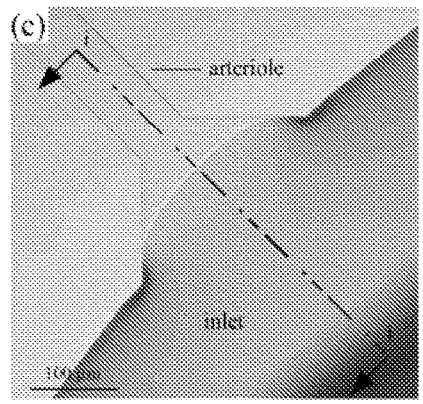 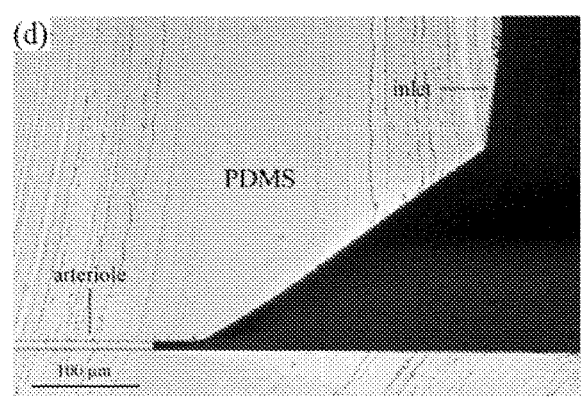
FIG. 2C    FIG. 2D

CAPILLARY NETWORK DEVICES AND METHODS OF USE

INCORPORATION BY REFERENCE

This application is a U.S. National Stage Application of PCT/US2013/042314, filed on May 22, 2013, which claims the benefit of the filing date of U.S. Provisional Application 61/650,283, filed on May 22, 2012. All of the aforementioned applications are incorporated herein by reference in their entireties.

FIELD OF THE DISCLOSURE

The present disclosure relates to Capillary Network Devices (CNDs). More particularly, the present invention relates to micro-scale devices that simulate the capillary networks and their physiological function (artificial microvascular devices).

BACKGROUND OF THE INVENTION

Human red blood cells in vivo are in a dynamic state. In whole blood, white blood cells are normally present in the range between 4,300 and 10,800 cells/μL and the normal RBC range at sea level is 5.4 million/μL (±0.8) for men and 4.8 million μL (±0.6) for women. The red blood cells contain hemoglobin, the iron-containing protein that carries oxygen throughout the body and gives red blood its color. The percentage of blood volume composed of red blood cells is called the hematocrit.

The normal life span of a red blood cell (RBC) is 120 days. Approximately 0.875% of the RBCs are retired every 24 hours by the spleen and new RBCs are made by the bone marrow. Consequently, when blood is drawn from a donor, there are a percentage of white blood cells and a spectrum of cells of different ages.

During the 6 weeks of conventional cold storage, there is a time-dependent deterioration of the biochemical, molecular, and mechanical properties of the RBCs collectively known as the "RBC storage lesion." Upon collection, whole blood is introduced to citrate phosphate dextrose (CPD), an acidic solution, which immediately lowers the blood pH to 7.1 from a normal pH of 7.4 and leads to the rapid breakdown of 2,3-diphosphoglycerate (2,3-DPG) within the RBC; by 2 weeks of storage, 2-3-DPG is undetectable. At 1-6° C., the metabolic processes of RBCs are not entirely halted. RBCs, suspended in dextrose, metabolize dextrose into adenosine 5'-triphosphate (ATP), 2,3-DPG and metabolic waste products, such as lactate. Reactive oxygen species (e.g. hydroxyl, peroxy, alkoxy radicals) are generated by the inability of the refrigerated RBC, which contains a highly reactive mixture of iron and oxygen, to maintain the iron atoms of hemoglobin (Hb) in a ferrous state.

The continual exposure of the RBCs to accumulated waste products and reactive oxygen species leads to a decrease in RBC deformability via an increase in membrane rigidity, a decrease in the surface area/volume ratio, and increase in intracellular viscosity. Progressive oxidative damage to the proteins, lipids and carbohydrates of the RBC membrane results in increased ion leaks (e.g., potassium) and loss of membrane by exocytosis (resulting in a gradual change in the morphology and size of the RBCs from 8 μm diameter biconcave disks to 5 μm diameter spherocytes), increased mean cell hemoglobin concentration, increased exposure of phosphatidylserine (PS, a known marker for RBC senescence and clearance from circulation) on the outer surface of the membrane—PS increases RBC adhesiveness to the endothelium and procoagulant activity—and increased osmotic fragility. These effects ultimately result in RBC apoptosis, hemolysis, and the accumulation of extracellular free hemoglobin in the bag. Oxidative damage to the RBCs increases the acidity and hyper-osmolality of the suspending storage media (with an end pH of ~6.6 and osmolality of ~320 mmol/kg at 6 weeks); the deteriorating RBCs are bathed in an increasingly toxic media. When transfused, intravascular hemolysis may occur, as well as acute hypertension, vascular injury, kidney dysfunction and/or rapid clearance from the circulation when transfused.

The RBC expends ATP in an attempt to repair its cellular components; however, without a nucleus, the protein synthesis needed to continually replace key enzymes within the RBC cannot occur throughout the duration of storage, so the cells become increasingly rigid and fragile. Storage induced biochemical and mechanical changes within the RBCs reduce their ability to undergo physiologically relevant deformations, increasing the overall viscosity of blood and decreasing microvascular perfusion (e.g., at bifurcations, non-deformable RBCs may bypass the narrow microchannels for the larger, high flow microchannels or even plug the narrow microchannels as seen in our devices) resulting in poor tissue oxygenation.

The primary physiologic function of red blood cells (RBCs) is to transport oxygen from the respiratory surfaces in the lungs to the metabolizing tissues and end organs. The level of local tissue oxygenation depends to a large degree on the dynamics of blood flow in microchannels of microvascular networks. To maintain adequate microvascular perfusion, RBCs must be able to continually deform at physiologically high hematocrit (Hct) concentrations, under a wide range of flow conditions, in vessels ranging from 3- to 8-μm microchannels to 50- to 100-μm arterioles and venules. Therefore, maintaining an appropriate level of "deformability" is crucial for RBC physiological function. The RBC's ability to undergo folding deformations when traversing narrow microchannels and shear-induced deformations of the kind experienced by RBCs in larger vessels, arterioles, and venules declines progressively in storage. Because of this storage-induced deterioration, stored RBCs may be unable to maintain adequate blood flow in microchannels and deliver oxygen as effectively as their fresh counterparts. If transfused, they may be unable to improve perfusion of the microvascular networks and oxygenation of tissues and, thus, may reduce the clinical efficacy of RBC transfusions. The least deformable stored RBCs are mechanically sensed and retained by the spleen and removed from circulation by the reticuloendothelial system shortly after transfusion.

The decline of RBC deformability during refrigerated storage is a very well-known part of "storage lesion" and has been previously extensively documented in studies employing a wide variety of existing methods. The comparison between fresh and stored RBCs to test the overall sensitivity of a CND of the disclosure is used in the context of RBC storage and transfusion (rather than to demonstrate the progressive deterioration of RBC mechanical properties occurring in storage).

Most of the existing tools for measuring the deformability of RBCs have been applied to stored cells including: 1) micropipette aspiration, 2) micropore filtration, 3) ektacytometry, 4) laser-assisted optical rotational cell analyzer (LORCA), 5) optical tweezers, and 6) RBC adhesion assay. Although very informative for studying the RBC rheologic response under well-defined conditions, these conventional approaches have several common limitations: 1) each technology is focused on a narrow subset from the wide spectrum of deformations experienced by RBCs in the microcirculation, 2) RBC properties are examined under nonphysiological conditions (e.g., at ultralow Hct or while suspended in high-viscosity buffers), and 3) the effects of the architecture of microvascular networks are not taken into account.

The flow of blood in actual microvascular networks has been found to exhibit chaotic temporal oscillations (Griffith, "Temporal Chaos in the Microcirculation," Elsevier, *Cardiovascular Research*, Vol. 31, p. 342-358, 1996). Kiani et al. proposed that such oscillations may occur in the absence of biological regulation and could result entirely from specific nonlinear rheological properties of blood within microvascular networks (Kiani et al., "Fluctuations in Microvascular Blood flow Parameters Caused by Hemodynamic Mechanisms," The American Physiological Society, p. H1822-H1828, 1994). However, direct validation of microvascular behavior using in vivo experiments may be prohibitively complex or even impossible. Thus, an in vitro model of microvascular networks is essential for critical evaluation and/or validation of existing theory, models and computer simulations.

Cokelet et al. described a simple modification of standard photolithography that was used to fabricate systems of interconnected microchannels (Cokelet et al., "Fabrication of in Vitro Microvascular Blood Flow Systems by Photolithography," *Microvascular Research*, Vol. 46, p. 394-400, 1993). This and other methods have been successfully adapted for production of flow systems that are used for endothelial cell culture (Frame et al., "A System for Culture of Endothelial Cells in 20-20-µm Branching Tubes," *Microcirculation*, Vol. 2, No. 4, p. 377-385, 1995; US Pat. Pub. 2002/0182241, Borenstein et al., 2002; U.S. Pat. No. 7,517,453, Bitensky, et al., 2009).

However, current instrumentation does not provide sufficient and adequate means to obtain actual information regarding the flow of blood in capillary network channels. Accordingly, there is a need for improved artificial microvascular network devices to simulate the microvascular system. There is a further need to be able to assess the quality of stored blood prior to transfusion into patients. In addition, there is a need to assess the deformability of a blood sample prior to preparing the blood for long term storage. Finally, there is a need to be able to identify blood subjected to long term storage that has an increased risk of adverse events when transfused into a patient.

SUMMARY OF THE INVENTION

The present disclosure includes and provides an artificial microvascular network device for a biological sample including a substrate having a capillary network having at least one microchannel of a variable size along its length, at least one inlet port in communication with the capillary network microchannel for sample entry, and at least one outlet port in communication with the capillary network microchannel for sample exit; where at least one microchannel ranges in size from 3 µm to 70 µm.

The present disclosure also includes and provides a capillary network device (CND) for a biological sample having a substrate; one or more inlet ports for sample entry formed on the substrate; one or more inlet microchannels formed on the substrate in communication with one or more inlet ports for sample entry; one or more outlet microchannels formed on the substrate in communication with one or more inlet microchannels; and one or more outlet ports formed on the substrate in communication with the one or more outlet microchannels; where the inlet microchannels and outlet microchannels have one or more dimensions of a variable size along their length ranging in size from 3 µm to 70 µm.

The present disclosure also includes and provides for a method comprising obtaining a blood sample from a unit of blood; applying the blood sample to a capillary network device (CND); measuring deformability in the blood sample and comparing the deformability to a predetermined value; and selecting the unit of blood for extended storage.

The present disclosure also includes and provides for a method comprising obtaining a blood sample from a unit of stored blood; applying the blood sample to a capillary network device (CND); measuring deformability in the blood sample and comparing said deformability to a predetermined value; and selecting the unit of stored blood for transfusion into a patient in need of a unit of blood.

These and other aspects of the invention will become apparent to one of skill in the art.

BRIEF DESCRIPTION OF THE DRAWINGS

FIGS. 2A-2G illustrate exemplary Capillary Network Device (CND) fabrication in accordance with an aspect of the disclosure.

FIGS. 11A-1C illustrate flow rates for anaerobically and aerobically stored blood obtained from CNDs according to exemplary aspects.

DETAILED DESCRIPTION

Figure 1A:
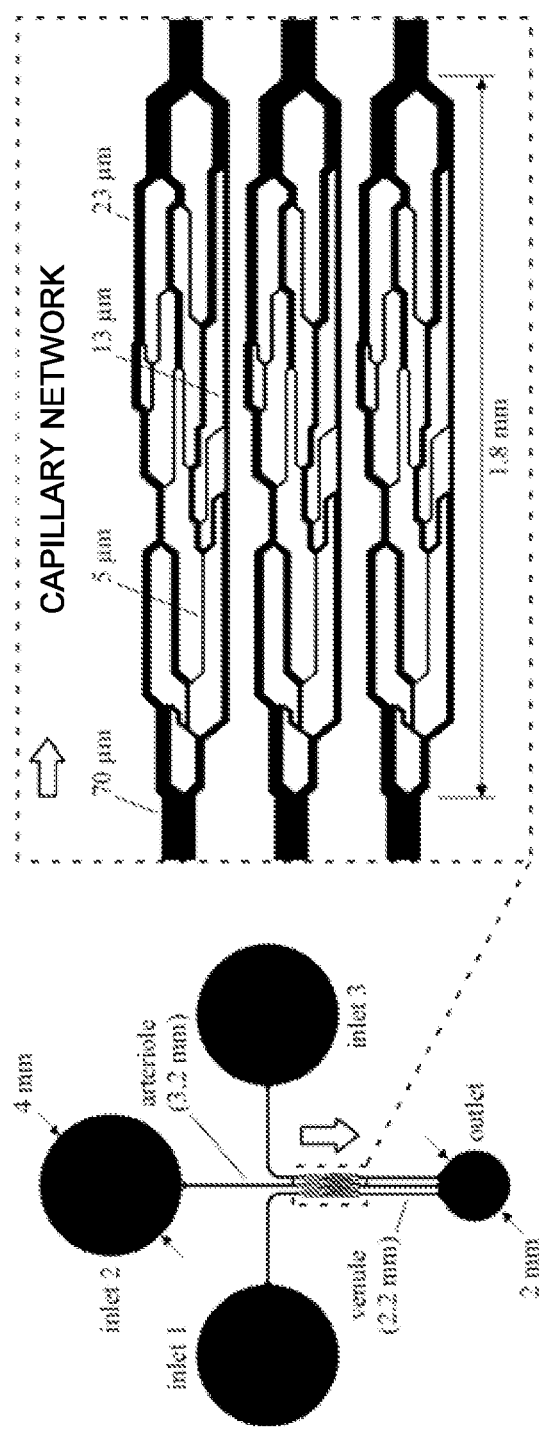
FIGS. 1A-1E illustrate exemplary Capillary Network Devices (CNDs) of the disclosure.

The transfusion of red blood cells (RBCs) is a life-saving therapy aimed at improving oxygenation of the tissues and vital end organs in severely anemic patients. The majority of RBC units used for transfusion are stored at 1-6° C. for up to 42 days in an oxygen-permeable polyvinylchloride blood bag that contains additive/preservative solution. In order for RBCs to perform their primary function, the delivery of oxygen, they must be able to perfuse vast networks of microvascular microchannels; however, oxidative damage experienced by the RBCs during hypothermic storage contributes to the progressive deterioration of the biochemical and mechanical properties of the stored RBCs, thereby decreasing their functional ability to perfuse microvascular networks.

Blood Donor: Whole blood is preferably donated from a healthy individual or donor and held in a blood bank for later use to be ultimately used by a recipient. Subjects who are scheduled for surgery or other treatment may donate blood for themselves in a process known as autologous blood donation. Alternatively, blood is donated for use by another in a process known as heterologous transfusion. The collection of a whole blood sample drawn from a donor, or in the case of an autologous transfusion from a patient, may be accomplished by techniques known in the art, such as through donation or apheresis.

Whole Blood: Whole blood is a suspension of blood cells that contains red blood cells, white blood cells, platelets suspended in plasma, including electrolytes, hormones, vitamins, and antibodies.

Blood products: As used herein, "blood product" or "blood products" refers to, and includes, whole blood, red blood cells, plasma, leukocytes, and platelets. "Blood product" also refers to depleted blood products including packed red blood cells, leukocyte reduced red blood cells, platelet reduced red blood cells. Blood products further include blood products having one or more additive solutions including, but not limited to, anticoagulants, antioxidants, storage additives, and buffers. Depleted blood products, as used herein, refer to blood products depleted of $O_2$, $CO_2$ or both, particularly after treatment with, or passage through a device of the present disclosure. Deoxygenated blood products are depleted blood products that have had oxygen levels restored to in vivo levels, or higher, usually in preparation for transfusion.

Red Blood Cells (RBCs): As used herein, "red blood cells" (RBCs), "packed red blood cells" (pRBCs), and "red blood cell suspensions" refer to and include blood products having red blood cells or erythrocytes. Red blood cells further include red blood cell products having one or more additive solutions. Red blood cells as used herein, may be depleted or reduced of leukocytes and other non-erythrocytes. As used herein, red blood cells include compositions depleted of plasma (plasma reduced). Red blood cells, as used herein, may further include red blood cell products having reduced or depleted platelets.

White blood cells: White blood cells or leukocytes as used herein include granulocytes also known as polymorphonuclear leukocytes. Granulocytes include neutrophils, basophils, and eosinophils. White blood cells also include agranulocytes, also known as mononuclear leukocytes, and include monocytes, and macrophages. Blood products according to the present disclosure include leukoreduced and leukodepleted blood.

Platelets: Platelets are small cellular components of blood that facilitate the clotting process by sticking to the lining of the blood vessels. The platelets, like the red blood cells, are made by the bone marrow and survive in the circulatory system for 9 to 10 days before they are removed by the spleen. Platelets are typically prepared using a centrifuge to separate the platelets from the plasma. Platelets, unlike RBCs, require $O_2$ for the generation of ATP.

Plasma: Plasma is a protein-salt solution and the liquid portion of the blood in which red and white blood cells and platelets are suspended. Plasma is 90% water and constitutes about 55 percent of the blood volume. One of the primary functions of plasma is to assist in blood clotting and immunity. Plasma is obtained by separating the liquid portion of the blood from the cells. Typically, plasma is separated from the cells by centrifugation. Centrifugation is the process used to separate the components of the whole blood into the plasma, the white blood cells, the platelets and the packed red blood cells. During centrifugation, the plasma will initially migrate to the top of a vessel during a light spin. The plasma is then removed from the vessel. The white blood cells and platelets are removed during a second centrifugation cycle to produce the packed red blood cells.

A venule as used in the present disclosure refers to an output microchannel that has a width of 50 to 100 µm and a depth of about 5 µm. A venule as used herein, also refers to output microchannels that have cross sectional areas of 300 to 30,000 µm$^2$. A venule as used herein, also refers to output microchannels having a diameter of 20 to 200 µm$^2$. An output channel is a channel having a width of greater than 100 µm and a depth of about 5 µm that provide for unrestricted flow and provide for connecting output ports from output microchannels of various dimensions.

An arteriole as used in the present disclosure refers to an input microchannel that has a width of 50 to 100 µm and a depth of about 5 µm. An arteriole as used herein, also refers to output microchannels that have cross sectional areas of 300 to 30,000 µm$^2$. An arteriole as used herein, also refers to output microchannels having a diameter of 20 to 200 µm$^2$. An input channel is a channel having a width of greater than 100 µm and a depth of about 5 µm that provide for unrestricted flow and provide for connecting input ports to input microchannels of various dimensions.

As used herein and in the appended claims, the singular forms "a," "an," and "the" include plural references unless the content clearly dictates otherwise. Thus, for example, reference to "a microchannel" includes a plurality of such microchannels and equivalents thereof known to those skilled in the art, and so forth, and reference to "the microchannel" is a reference to one or more such microchannels and equivalents thereof known to those skilled in the art, and so forth.

The present disclosure provides for, and includes Capillary Network Devices (CNDs) and artificial microvascular network (AMVN) devices, and related methods of making and methods of using such devices. The present disclosure generally relates to a CND or an AMVN device comprising a substrate including a capillary network configured so as to simulate those actually encountered in the circulation of various humans and animal model systems. In certain aspects, the CND or AMVN devices may be used to investigate the effect of storing RBCs under aerobic and anaerobic conditions. In other aspects, the CND or AMVN devices may be used to assess the quality of RBCs prior to storing under aerobic or anaerobic conditions. In other aspects, the CND or AMVN devices may be used to assess the quality of RBCs after storage to select for stored blood suitable for transfusion into a patient in need. However, the use of such CND or AMVN devices is not so limited.

The present disclosure provides for, and includes a CND generally comprising a substrate having at least one inlet port, at least one outlet port, and a capillary network formed thereon. More particularly, the AMVN device comprises: a substrate; a capillary network comprised of at least one microchannel of a variable size; at least one inlet port to the capillary network microchannel for sample entry; and at least one outlet port from the capillary network microchannel for sample exit. Further, the capillary network may generally be formed as at least one, or a series of, microchannels ranging in size, e.g., from 3 μm (microchannels) to 70 μm (arteriole, venule), which may have a variable cross-section shape and/or size along their length, and may be arranged in a pattern based on the topologic organization of in vivo microvasculature.

In certain aspects, the capillary network may comprise an array of microchannels connected by a series of inlet channels and outlet channels. In other aspects, the capillary network may comprise an array of microchannels connected by a series of inlet microchannels and outlet microchannels. The microchannels may have a uniform width along their length or may vary in width along their length. In certain aspects, microchannels may include branches along their length of varying widths, or may include portions of varying width along their length. For instance, the microchannels may taper along their length (e.g., gradually taper, sharply taper, etc.) or may be formed as a branched network comprising an array of varying widths. The capillary network units may be connected to one or more inlet ports via one or more inlet channels or via larger microchannels (arterioles). The capillary network units may be connected via one or more outlet channels or via larger microchannels (venules) to one or more outlet ports. The depth of all microchannels may be prepared to any desired depth throughout the CND, e.g., about 3 μm to about 8 μm, about 5 μm, etc.

The CND may comprise one or a series of identical capillary network arrays, each connected by an arteriole (e.g., an input microchannel of 50 to 100 μm) to an independent inlet (directly or through an inlet channel), and by a venule (e.g., an output microchannel of 50 to 100 μm) to a common outlet port (directly or through an outlet channel). In certain aspects, the dimensions of the arterioles (as well as of the venules) may be generally the same so as to match the nominal fluidic resistance of the independent capillary network arrays.

In aspects according to the present disclosure, a CND design may comprise one or a series of independent, capillary network arrays, including identical arrays, to enable testing of discrete samples, e.g., under the same conditions simultaneously. In other aspects, a CND may comprise two or more capillary network arrays having different microchannel arrays to provide for comparison of capillary network designs. Various numbers and configurations are within the scope of the disclosure. In an aspect, a CND may include a single array. In another aspect, a CND may include two arrays each having an independent inlet port. In another aspect, a CND may include two arrays having a common inlet port. In an aspect, a CND may include three arrays, each having an independent inlet port. In some aspects, a CND may include three arrays having a common inlet port. In some aspects, a CND may include four arrays, each with an independent inlet port. In yet other aspects, a CND may include five, six or more arrays, each array having an independent inlet port. In certain aspects, a CND may include both arrays with independent inlet ports and common inlet ports. By way of example, the use of more than one capillary network array may allow for comparison between, e.g., 1) stored RBCs washed and resuspended in their own storage medium, 2) stored RBCs washed and suspended in saline, and 3) fresh RBCs washed and suspended in saline, etc. In other aspects, CNDs having multiple arrays may provide for testing of multiple samples and include standardized control samples.

With reference to FIG. 1A, in one aspect, the CND (the "AMVN device"), may be comprised of a series of branched capillary network arrays arranged in parallel. An AMVN device is a CND incorporating one or more bifurcations of an inlet microchannel into microchannels and one or more convergences of microchannels into an outlet microchannel. In certain aspects of the present disclosure, an AMVN device may include arrays of parallel microchannels of varying dimension. In some aspects, an AMVN device is a CND incorporating one or more bifurcations into two microchannels of unequal dimension. In some aspects, an AMVN device is a CND incorporating one or more convergences of two microchannels of unequal dimension. Each capillary network array may include branched microchannels of varying widths ranging from, e.g., about 3 μm (microchannels) through to about 70 μm or more (arteriole, venule), e.g., about 5 μm to about 13 μm to about 23 μm to about 70 μm, etc. By way of non-limiting example, as illustrated, the AMVN device may comprise, e.g., thirty-four 5-mm-deep microchannels ranging in width from 5 to 70 μm. As illustrated, the device design may comprise three independent, identical capillary network arrays to enable testing of three samples under the same conditions simultaneously. The capillary network units may be connected via one or more inlet ports by inlet channels that may be 1-5 mm long, 1-4 mm long, 4 mm long, etc. The capillary network units may be connected via larger microchannels (e.g., arterioles that are 1-4 mm long, 1-3.5 mm long, 3.2 mm long, etc.). In further aspects, the capillary network units may be connected and via outlet channels that may be 1-5 mm long, 1-4 mm long, 4 mm long, etc. In certain aspects, capillary network units may be connected by venules that are 1-4 mm long, 1-3.5 mm long, 2.2 mm long, etc. to one or more outlet channels that may be 1-5 mm long, 1-4 mm long, 1-3 mm long, 2.2 mm long, etc. The capillary network units may be connected to one or more inlet ports directly by an input channel. The capillary network units may be connected to one or more inlet ports indirectly by an input microchannel through an input channel. The capillary network units may be connected to one or more inlet ports directly through an input channel. The capillary network units may be connected to one or more outlet ports directly by an output channel. The capillary network units may be connected to one or more outlet ports indirectly by an output microchannel through an output channel. The capillary network units may be connected to one or more outlet ports directly through an output channel. The depth of all microchannels may be prepared to any desired depth throughout the CND, e.g., about 3 μm to about 10 μm, about 5 μm, etc.

The present disclosure provides for and includes CNDs having microchannels of one or more dimensions. As used herein, a dimension of a microchannel may be provided as a width, depth, and length. In some aspects, a dimension of a microchannel may be defined by a diameter of a microchannel. In other aspects, a dimension of a microchannel may be defined by a cross-sectional area. In yet other aspects, a dimension of a microchannel may be defined by a volume of said microchannel. As provided in the examples and description below, the dimensions of the microchannels are provided as a width, depth and length. As appropriate, the dimensions may be converted into other geometries.

In aspects according to the present disclosure, microchannels may have different cross sectional shapes. In some aspects, a microchannel may have a rectangular shape. In some other aspects, a microchannel may have a rectangular shape with rounded edges. In certain aspects, the microchannels may be prepared having circular or oval cross-sectional shapes. In accordance with the present disclosure, round or oval shaped microchannels can have cross-sectional areas as defined by the widths and depths above. In other aspects, a width and depth may be converted to a cross-sectional area and the corresponding circular or oval shaped microchannel prepared. In some aspects, a microchannel has a depth that is less than the width. In some other aspects, the depth of a microchannel is about equal to the width. In certain aspects, the depth of a microchannel does not depend on the width and any of the depths recited above can be in used in combination with the widths provided above to prepare microchannels with desired cross-sectional areas.

In aspects according to the present disclosure, microchannels may have a constant depth. In certain aspects, microchannels can be prepared having a constant depth that varies 1 µm to 25 µm. In some aspects, a microchannel depth may be from 2 µm to 20 µm. In other aspects, a microchannel depth may range from 3 µm to 15 µm, from 3 µm to 12 µm, from 3 µm to 10 µm, from 3 µm to 8 µm, or from 3 µm to 5 µm. In certain aspects, the depth of a microchannel is at least 2 µm, at least 3 µm, at least 5 µm, or at least 10 µm. In certain aspects, the depth is not less than 3 µm. In an aspect, the depth of a microchannel is about 5 µm. In another aspect, the depth of the microchannel is about 8 µm. In yet another aspect, the depth of the microchannel is about 10 µm. In certain aspects, the depth is less than about 3 µm. In an aspect, the depth of a microchannel is less than about 5 µm. In another aspect, the depth of the microchannel is less than about 8 µm. In yet another aspect, the depth of the microchannel is less than about 10 µm.

Microchannels according the present disclosure can vary in width from 3 µm to 100 µm wide. In some aspects, a microchannel ranges from 3 µm to 70 µm wide. In other aspects, a microchannel ranges from 3 µm to 50 µm, from 3 µm to 25 µm, from 3 µm to 15 µm, or from 3 µm to 10 µm wide. In certain aspects, a capillary network includes one or more microchannels of at least 5 µm, 13 µm, 23 µm, and 70 µm wide.

As provided in the present disclosure, CNDs may comprise an array of microchannels connected to at least one inlet port and at least one outlet port. In certain aspects, at least one inlet microchannel is a primary inlet microchannel in communication with one or more microchannel junctions to bifurcate a primary inlet microchannel into at least two secondary inlet microchannels. In other aspects, a secondary inlet microchannel is in communication with at least one microchannel junction to bifurcate a secondary inlet microchannel into at least two tertiary inlet microchannels. In some aspects, a tertiary inlet microchannel is in communication with at least one microchannel junction to bifurcate a tertiary inlet microchannel into at least two quaternary inlet microchannels.

In some aspects, a primary inlet microchannel can vary in size from 50 µm to 100 µm wide. In other aspects, a primary microchannel can range in size from 65 µm to 95 µm, from 70 µm to 85 µm, or from 75 µm to 80 µm wide. In certain aspects, a size of the primary inlet microchannel is at least 50 µm or in other aspects at least 100 µm wide. In other aspects, a size of a primary inlet microchannel is not less than 70 µm wide. In yet other aspects, a size of a primary inlet microchannel is not less than 50 µm wide.

In other aspects, a size of primary inlet microchannel is selected from a group consisting of 50 µm, 55 µm, 60 µm, 65 µm, 70 µm, 75 µm, 80 µm, 85 µm, 90 µm, 95 µm, and 100 µm wide. In some other aspects, a size of primary inlet microchannel is selected from a group consisting of 65 µm, 66 µm, 67 µm, 68 µm, 69 µm, 70 µm, 71 µm, 72 µm, 73 µm, 74 µm, and 75 µm wide. In one aspect, the size of primary inlet microchannel is about 70 µm wide.

In some aspects, a secondary inlet microchannel can vary in size from 5 µm to 50 µm wide. In an aspect, a secondary inlet microchannel may be 5 µm wide. In other aspects, a secondary microchannel ranges in size from 5 µm to 10 µm, from 5 µm to 15 µm, from 5 µm to 20 µm, from 20 µm to 45 µm, from 25 µm to 40 µm, or from 30 µm to 35 µm wide. In certain aspects, a size of the secondary inlet microchannel is at least 20 µm wide or in other aspects at least 25 µm wide. In other aspects, a size of the secondary inlet microchannel is not less than 15 µm wide. In yet other aspects, a size of the secondary inlet microchannel is not less than 20 µm wide.

In other aspects, a size of secondary inlet microchannel is selected from a group consisting of 5 µm, 10 µm, 15 µm, 20 µm, 25 µm, 30 µm, 35 µm, 40 µm, 45 µm, 50 µm, 55 µm, and 60 µm wide. In some other aspects, a size of secondary inlet microchannel is selected from a group consisting of 5 µm, 10 µm, 15 µm, 16 µm, 17 µm, 18 µm, 19 µm, 20 µm, 21 µm, 22 µm, 23 µm, 24 µm, 25 µm, 26 µm, 27 µm, 28 µm, 29 µm, and 30 µm wide. In an aspect, a size of secondary inlet microchannel is 23 µm wide. In another aspect, a size of a secondary inlet microchannel is 5 µm wide.

In some aspects, a tertiary inlet microchannel can vary in size from 5 µm to 25 µm wide. In other aspects, a tertiary microchannel ranges in size from 8 µm to 23 µm, from 11 µm to 20 µm, or from 13 µm to 16 µm wide. In certain aspects, a size of the tertiary inlet microchannel is at least 10 µm or in other aspects at least 15 µm wide. In other aspects, a size of the tertiary inlet microchannel is not less than 15 µm wide. In yet other aspects, a size of the tertiary inlet microchannel is not less than 10 µm wide. In yet another aspect, a size of the tertiary inlet microchannel is not less than 5 µm wide.

In other aspects, the size of tertiary inlet microchannel is selected from the group consisting of 3 µm, 5 µm, 8 µm, 9 µm, 10 µm, 11 µm, 12 µm, 13 µm, 14 µm, 15 µm, 16 µm, 17 µm, 18 µm, 19 µm, and 20 µm wide. In one aspect, the size of tertiary inlet microchannel is 13 µm wide. In one aspect, the size of tertiary inlet microchannel is 5 µm wide.

In some aspects, a quaternary inlet microchannel can vary in size from 3 µm to 20 µm wide. In other aspects, a tertiary microchannel ranges in size from 5 µm to 17 µm, from 8 µm to 14 µm, or from 10 µm to 12 µm wide. In certain aspects, a size of a tertiary inlet microchannel is at least 3 µm or in other aspects at least 5 µm wide. In other aspects, a size of the tertiary inlet microchannel is not less than 3 µm. In yet other aspects, a size of the tertiary inlet microchannel is not less than 5 µm wide.

In other aspects, a size of tertiary inlet microchannel is selected from a group consisting of 2 µm, 3 µm, 4 µm, 5 µm, 6 µm, 7 µm, 8 µm, 9 µm, 10 µm, 11 µm, 12 µm, 13 µm, 14 µm, and 15 µm wide. In one aspect, the size of tertiary inlet microchannel is 5 µm wide.

Figure 1B:
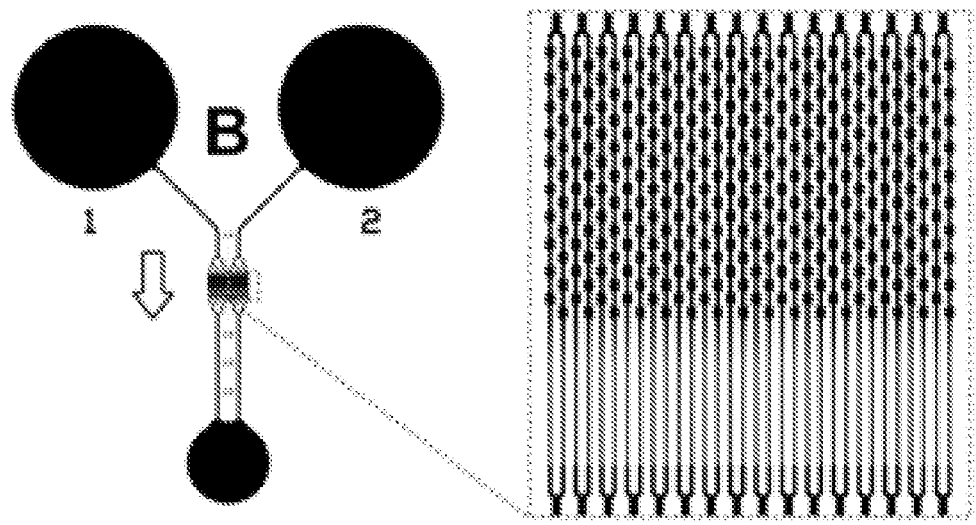
Figure 1C:
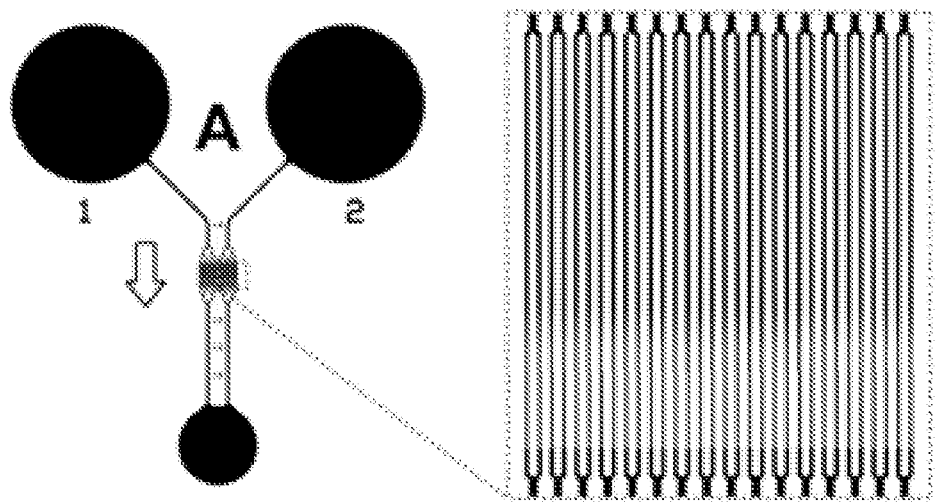

In other aspects according to the present disclosure, for example with reference to FIGS. 1B and 1C, a CND may comprise a series of capillary network arrays including two or more parallel microchannels of varying width. In an aspect, a CND may include 5 or more parallel microchannels. In other aspects, a CND may include 10 or more parallel microchannels. In another aspect, a CND may include 15 or more parallel microchannels. In another aspect, a CND may include 20 or more parallel microchannels. In another aspect, a CND may include 25 or more parallel microchannels. In another aspect, a CND may include 15 or more parallel microchannels. As illustrated in FIGS. 1B and 1C, a CND may include 16 parallel microchannels.

The present disclosure provides for, and includes, CNDs having 5 to 50 parallel microchannels. In an aspect, a CND may include 5 to 25 parallel microchannels. In other aspects, a CND may include 10 to 25 parallel microchannels. In another aspect, a CND may include 10 to 20 parallel microchannels. In another aspect, a CND may include 10 to 18 parallel microchannels. In another aspect, a CND may include 8, 16, 24, 32, or more parallel microchannels. In another aspect, a CND may include 16 or 32 parallel microchannels.

The CNDs of the present disclosure include and provide for microchannels having an overall length as measured from an inlet port to an outlet port of 3 µm to about 3000 µm. The CNDs of the present disclosure include and provide for microchannels having an overall length as measured from an inlet channel to an outlet channel of 3 µm to about 3000 µm. In some aspects, the total length of a branched microchannel array, traced from a first input microchannel of less than 150 µm to a first output microchannel of greater than 150 um may be from 3 µm to about 3000 µm. In some aspects, parallel and branched microchannels of the present disclosure may be from 3 µm to 300 µm long. In other aspects, parallel and branched microchannels may be from 300 µm to 3,000 µm long. In certain aspects, parallel and branched microchannels may be from 100 µm to 500 µm long. In some aspects, parallel and branched microchannels may be from 200 µm to 500 µm long. In yet other aspects, parallel and branched microchannels may be from 300 µm to 500 µm long or from 300 µm to 1000 µm long. In further aspects, the length of parallel and branched microchannels may be combinations of various lengths selected from a group consisting of 3 µm to 300 µm, 3 µm to 500 µm, 3 µm to 750 µm, 3 µm to 1000 µm, 3 µm to 1500 µm, 3 µm to 2000 µm, 3 µm to 2500 µm, and 3 µm to 3000 µm. In some aspects, the length of parallel and branched microchannels may be combinations of various lengths selected from a group consisting of 100 µm to 300 µm, 100 µm to 500 µm, 100 µm to 750 µm, 100 µm to 1000 µm, 100 µm to 1500 µm, 100 µm to 2000 µm, 100 µm to 2500 µm, and 100 µm to 3000 µm. In other aspects, the length of parallel and branched microchannels may be combinations of various lengths selected from a group consisting of 300 µm to 500 µm, 300 µm to 750 µm, 300 µm to 1000 µm, 300 µm to 1500 µm, 300 µm to 2000 µm, 300 µm to 2500 µm, and 300 µm to 3000 µm.

In aspects according to the present disclosure, a CND having two or more parallel microchannels with varying width may have microchannels with a straight portion, a tapered portion and a constant portion. For example, as shown in FIGS. 1B and 5E, a microchannel may include, e.g., a 5 µm wide straight portion along its length of about 100 µm to about 400 µm, e.g., about 330 µm, followed by a portion that gradually tapers along its length of about 10 µm to about 50 µm, e.g., 45 µm, to a, e.g., 3 µm wide constant portion along its length of about 100 µm to about 400 µm, e.g., about 125 µm. Again, the depth of all microchannels may be prepared to any desired depth throughout the CND, e.g., about 3 µm to about 8 µm, about 5 µm, etc.

In aspects according to the present disclosure, the length of a straight portion of a microchannel in a CND may be from 5 to 400 µm. In other aspects, a length of a straight portion may be from 25 to 400 µm, 50 to 400 µm, 100 to 400 µm or 200 to 400 µm. In some other aspects, a length of a straight portion of a microchannel may be at least 100 µm, at least 150 µm, at least 200 µm, at least 250 µm, at least 300 µm, or at least 350 µm. In other aspects, a length of a straight portion of a microchannel is not more than 400 µm or not more than 350 µm. In still other aspects, a length of a straight portion of a microchannel may be selected from the group consisting of 100 µm, 200 µm, 250 µm, 300 µm, 330 µm, 350 µm and 400 µm. In some other aspects, a length of a straight portion of a microchannel is 200 µm. In another aspect, a length of a straight portion may be 250 µm. In some other aspects, a length of a straight portion of a microchannel is 300 µm. In another aspect, a length of a straight portion may be 330 µm. In yet other aspects, a length of a straight portion of a microchannel is 350 µm.

In aspects according the present disclosure, a straight portion of a microchannel in a CND may be from 3 to 50 µm wide. In some aspects, a straight portion of a microchannel may be 3 to 25 µm wide. In another aspect, a straight portion of a microchannel may be 5 µm wide. In some aspects, a straight portion of a microchannel may be 6 µm wide. In other aspects a straight portion of a microchannel may be 7 µm wide. In yet another aspect, a straight portion of a microchannel may be 8 µm wide. In certain aspects of the present disclosure, a straight portion of a microchannel may be less than 8 µm wide.

In aspects according to the present disclosure, a length of a tapered portion of a microchannel in a CND may be between 10 to 75 µm long. In other aspects, a length of a tapered portion may be from 5 to 100 µm, 5 to 50 µm, 5 to 75 µm or 10 to 75 µm long. In some other aspects, the length of a tapered portion of a microchannel may be at least 10 µm, at least 20 µm, at least 40 µm, at least 50 µm, at least 60 µm, or at least 80 µm. In other aspects, a length of a tapered portion of a microchannel is not more the 100 µm or not more than 75 µm. In still other aspects, a length of a tapered portion of a microchannel may be selected from the group consisting of 20 µm, 30 µm, 35 µm, 40 µm, 45 µm, 50 µm and 55 µm. In some other aspects, a length of a tapered portion of a microchannel is 45 µm. In another aspect, a length of a tapered portion may be 50 µm.

In aspects according to the present disclosure, a tapered region may gradually taper along the length of its tapered portion (e.g. the taper length) from about 30 µm to about 3 µm. In certain aspects, a tapered region may taper from about 5 µm to about 3 µm over its taper length. In some aspects, the taper may be from about 8 µm to about 5 µm. In other aspects, the taper may be from about 8 µm to about 3 µm of its taper length.

In aspects according to the present disclosure, the length of a constant region of a microchannel in a CND following a tapered region may be from 100 to 400 µm. In other aspects, the length of a constant region may be from 75 to 150 µm, 100 to 150 µm, 75 to 140 µm or 100 to 200 µm. In some other aspects, the length of a constant region of a microchannel is at least 50 µm, at least 75 µm, at least 100 µm, at least 125 µm, or at least 150 µm. In other aspects, the length of a constant region of a microchannel is not more than 150 µm or not more than 125 µm. In still other aspects, the length of a constant region of a microchannel is selected from the group consisting of 75 µm, 100 µm, 125 µm, 150 µm, 200 µm, and 250 µm.

In aspects according the present disclosure, a constant region of a microchannel in a CND following a tapered region may be from 3 to 10 µm wide. In some aspects, a constant region of a microchannel may be 3 to 8 µm wide. In another aspect, a constant region of a microchannel may be 5 µm wide. In some aspects, a constant region of a microchannel may be 3 µm wide. In other aspects a constant region of a microchannel may be 3 to 4 µm wide. In yet another aspect, a constant region of a microchannel may be 3 to 5 µm wide. In certain aspects of the present disclosure, a constant region of a microchannel may be less than 5 µm wide.

In aspects according to the present disclosure, the microchannels may include a series of one or more constrictions and expansions separated by a spacer region. In an aspect with reference to FIGS. 1C and 5G, a microchannel may include a 5 µm wide constriction, a 16 µm spacer, and an 11 µm expansion. In further reference to FIG. 1C, a microchannel may include 10 constriction, spacer and expansion features in series. In certain aspects, the series of expansions and constrictions may further include a gradually tapering region. As shown in FIG. 1C, a microchannel may taper from 5 µm to 3 µm over a length of 45 µm. In aspects according to the present disclosure, the tapering region may be followed by a constant region connected to one or more output microchannels. As shown in FIG. 1C, a constant region may be 125 µm long and 3 µm in width.

In aspects according to the present disclosure, the expansions may be from 6 to 23 µm wide. In an aspect, the expansion may be, e.g., 11 µm wide expansions separated by a spacing of about 10 µm to about 30 µm, e.g., 16 µm, along a gradually tapering length of about 10 µm to about 50 µm, e.g., 45 µm, to a, e.g., 3 µm wide portion along its length of about 100 µm to about 400 µm, e.g., about 125 µm. Again, the depth of all microchannels may be as prepared to any desired depth throughout the CND, e.g., about 3 µm to about 8 µm, about 5 µm, etc.

In aspects according to the present disclosure, expansions may be from 6 to 23 µm wide. In other aspects, an expansion may be from 9 to 20 µm, or 12 to 17 µm wide. In other aspects, the width of an expansion may be selected from the group consisting of 8 µm, 9 µm, 10 µm, 11 µm, 12 µm, 13 µm, 14 µm, 15 µm, and 20 µm. In yet other aspects, an expansion may be at least 50% wider than the spacer between two expansions. In other aspects, an expansion may be at least 75%, at least 100%, or at least 125% wider than the spacer. In other aspects, the expansion may be 150% wider than the spacer. In another aspect the expansion may be twice as wide or more. In a further aspect the expansion may be at least three times wider than the spacer region between expansions.

In an aspect, an expanded region of a microchannel in a CND according the present disclosure may be from 5 to 10 µm long. In an aspect, an expanded region may be 5 to 20 µm long. In other aspects, an expanded region may be about 10 µm, about 15 µm, or about 20 µm long. In aspects according to the present disclosure, an expanded region may be up to 10 µm long. In another aspect, an expanded region may be up to 15 µm long. In yet another aspect, the expanded region may be less than 20 µm.

The present disclosure further provides for spacer regions separating expanded regions. As illustrated in FIG. 5G, an 11 µm wide expansion may be separated by a spacing of about 16 µm. In other aspects according to the present disclosure, a spacing region may be from 10 µm to about 30 µm. In some embodiments, a spacing region may be from 5 to 10 µm, 5 to 15 µm, 5 to 20 µm, or 5 to 30 µm long. In other embodiments, a spacing region may be up to 20 µm long.

In aspects according to the present disclosure, a length of a spacer region between two expansions may be from 5 to 50 µm. In other aspects, the length may be from 7 to 30 µm, 9 to 20 µm, or 11 to 15 µm. In some other aspects, the length of a spacer between two expansions is at least 5 µm, at least 10 µm, at least 15 µm, at least 20 µm, or at least 25 µm.

In other aspects, the length of a spacer between two expansions is not more the 25 µm or not more than 15 µm. In still other aspects, the length of a spacer is selected from the group consisting of 9 µm, 10 µm, 11 µm, 12 µm, 13 µm, 14 µm, 15 µm, 16 µm, 17 µm, 18 µm, 19 µm, 20 µm, and 25 µm.

In aspects according to the present disclosure, the length of a constant region of a microchannel in a CND following a series of constrictions and expansions may be from 5 to 200 µm. In other aspects, the length of a constant region may be from 10 to 100 µm, 15 to 75 µm, 20 to 50 µm or 25 to 45 µm. In some other aspects, the length of a constant region of a microchannel is at least 10 µm, at least 25 µm, at least 50 µm, at least 75 µm, or at least 100 µm. In other aspects, the length of a constant region of a microchannel is not more the 200 µm or not more than 75 µm. In still other aspects, the length of a constant region of a microchannel is selected from the group consisting of 10 µm, 20 µm, 25 µm, 30 µm, 35 µm, 40 µm, 45 µm, 50 µm, 55 µm, 75 µm, 100 µm, 150 µm, and 200 µm.

In aspects according to the present disclosure, a CND may include more than 100 expanded regions (e.g., a an expansion paired with a constriction) in a microchannel. In certain aspects, the number of expanded regions may be less than 100. In other aspects, the number of expanded regions may be from 1 to 50. In an aspect, CND may have from 1 to 20 expanded regions. In another aspect, a CND may have from 5 to 15, or 10 to 20 expanded regions. In yet another aspect, a CND may have from 15 to 25, or 15 to 30 expanded regions. In certain aspects, a CND may have 5 expanded regions. In an aspect, a CND may have 10 expanded regions. In yet other aspects, a CND may have 15 expanded regions. In certain aspects, a CND may have 25 expanded regions. In an aspect, a CND may have 30 expanded regions. In yet other aspects, a CND may have 355 expanded regions. In other aspects, the number of expanded regions on a microchannel may be from 2 to 18, 4 to 16, 6 to 14, or 8 to 12. In some other aspects, number of expanded regions on a microchannel may be not less than 2, not less than 5, not less than 10, or not less than 15. In certain other aspects, the number of expansions on a microchannel is selected from the group consisting 2, 3, 4, 5, 6, 7, 8, 9, 10, 12, 14, 16, 18, and 20.

The present disclosure further provides for and includes CNDs having one or more parallel microchannels that combine one or more expanded regions with one or more tapered regions with constant regions and spacing regions.

In aspects according to the present disclosure, microchannel arrays of the CNDs may include more than one microchannel in communication with an inlet port. In an aspect, the inlet port may directly connect to two or more microchannels of the present disclosure. In an aspect, an inlet port may indirectly connect to two or more microchannels of the present disclosure by one or more inlet channels. In an aspect the inlet port may include a single larger input microchannel (e.g., an arteriole of 50 to 100 µm or larger) or input channel having bifurcations or forks to direct flow into a microchannel array of the present disclosure.

The substrate of the CND may be comprised of glasses, crystals, Si wafers, plastics, thermoplastics, waxes, gels, hydrogels, polymers, metals, ceramics, organic materials, inorganic materials, and any combinations thereof. A preferred substrate is transparent. Any suitable material for the capillary network microchannel may be used, and any suitable fabrication may be used, e.g., lithography described herein. However, neither the substrate nor the capillary network material is limited.

In certain aspects, the CND may be used to perform an integrative assessment of deformability of stored RBCs by measuring their effective ability to perfuse a CND described herein. In certain aspects, RBCs and other biological samples may be passed through the CND under a constant pressure difference between an inlet port and an outlet port of the device, and the overall rate of flow in the arteriole (or venule) of the CND may be quantified. A major advantage of this approach (with respect to existing technologies) is that in a single measurement the CND subjects RBCs to a wide range of physiologically relevant deformations (folding in microchannels and shear-induced deformations in larger vessels), under a variety of flow conditions (fast flow in some microchannels, slow or even intermittent flow in others) as they traverse the network of microchannels at physiological Hct concentrations (which enables cell-cell interactions).

In certain aspects, multiple samples may be analyzed simultaneously, under nearly identical conditions. In this aspect, a CND of the disclosure may be used, for example, to analyze side by side the effect of different experimental storage conditions or rejuvenation strategies on the rheologic properties of RBCs, e.g., stored for a specific period of time, under specific storage conditions, etc. In addition to these cross-sectional comparisons, a CND of the disclosure may also be used in longitudinal (time-course) studies of the effect of blood collection and component processing protocols, additive solutions, and storage conditions on deterioration of RBC deformability in storage.

In aspects according to the present disclosure, a CND provides for methods for evaluating the rheologic properties of RBCs under conditions that approximate the mechanical microenvironment of in vivo microcirculation closer than other existing techniques. The device is able to detect the storage-induced deterioration of RBC rheologic properties and to demonstrate an improvement in deformability of stored RBCs from units nearing expiration after washing in normal saline. The CND is helpful in developing and identifying better RBC storage conditions and rejuvenation strategies.

Figure 1D:
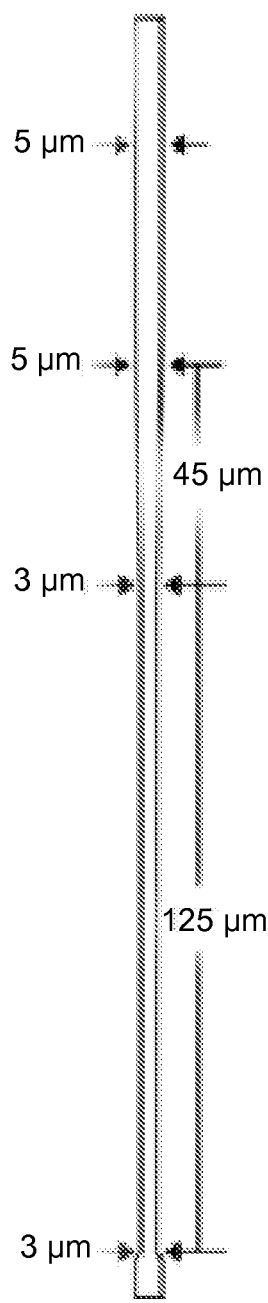

CNDs for measuring the mechanical properties of RBCs, particularly stored RBCs are included and provided in the present disclosure. The design of these devices are similar but for the configuration of capillary network arrays. As illustrated in the examples, each device includes identical capillary network arrays, and each capillary network array includes parallel array of microchannels, e.g., 32 parallel microchannels, each with a width of 5 µm that gradually taper to a width of 3 µm (with a universal height of 5 µm). With reference to FIG. 1D, a CND may be comprised of generally straight microchannels that gradually taper, whereas, with reference to FIG. 1E, a CND may be comprised of straight channels having a series of repeating 5 µm wide constrictions and 11 µm wide expansions that then gradually taper. RBC samples may be passed through the networks at a physiologically-relevant hematocrit and constant pressure. Both devices are designed as a test of the ability of individual RBCs in mass succession to squeeze through tiny microchannels in near-physiological conditions. Development of the devices and tests of their sensitivity to the mechanical properties, namely deformability, of RBCs are described below in the examples.

The devices are used to measure the storage-induced decline in the ability of RBCs, stored aerobically (control, FDA-standard) and anaerobically (test), to perfuse capillary networks in vitro and took measurements of flow rate in the venules (bulk flow) and microchannels (capillary flow) of the networks.

In a dual-arm, double-blinded cross-over clinical study, two RBC units are collected (on separate occasions) from each donor ($n_{donor}$=8 matched pairs, $n_{unit}$=16); one unit is stored aerobically and the other anaerobically. The aerobic RBC unit (control) is collected, processed, and stored for 9 weeks at 1-6° C. according to standard procedures. The anaerobic RBC unit (test) was additionally passed through an experimental device to completely deoxygenate RBCs, and stored in the same storage medium as the aerobic RBC unit (AS-3), but in an experimental oxygen-impermeable bag. Both units were sampled on Days 0, 21, 42, and 63 ($n_{sample}$=64) for mechanical testing. The hematocrit of each sample was adjusted to 40%, passed the samples through the microfluidic devices, and the rate of blood flow through each capillary was measured as well as the overall bulk flow rate through the device.

The overall rate of blood flow through the capillary network devices (a composite metric of RBC mechanical properties) was found to decrease progressively throughout storage, declining by ~19% for RBCs stored anaerobically and by ~28% for conventional storage on Day 42. The overall flow rate for anaerobic RBCs was consistently higher than for RBCs stored conventionally throughout the whole duration of storage, with the largest difference of 15% on Day 42. Although, the frequency of capillary plugging increased gradually for both types of storage, the plugging frequency was significantly lower for RBCs stored anaerobically compared to RBCs stored conventionally (about 45% difference on Days 21, 42 and 63 of storage).

The results indicate that anaerobic storage reduces the deleterious effect of hypothermic storage on mechanical properties of stored RBCs, and that this beneficial effect occurs in part due to a significant reduction in the number of cells in the population that are capable of plugging narrow microchannels. Without intending to be limited by theory, it is also determined that a CND of FIG. 1C (CND-B) is more sensitive to storage-induced decline in RBC deformability than CND of FIG. 1B (CND-A). Again, without intending to be limited by theory, this is believed due to the mechanical "exercising" of the cells (or loss of ATP) as the cells change deformational conformation passing in and out of the stenotic areas of the narrow 3 µm channels. This surprising insight into the effect of hypothermic storage on RBC properties and the design of AMVN capillary networks developed in this study are useful for assessing and developing improved RBC storage conditions, additive solutions and rejuvenation strategies to ensure the safety and efficacy of the blood supply.

The present disclosure provides for and includes methods for identifying units of blood collected for transfusion that are suitable for extended storage. In an aspect according to the present disclosure, a sample of blood obtained from a unit of blood collected for transfusion is applied to a CND of the present disclosure and the deformability is determined. In an aspect, the deformability is compared to the deformability of a standard sample and samples having deformability properties equal to or greater than the standard sample is selected for extended storage.

In aspects according to the present disclosure, deformability is determined as a normalized deformability (e.g., deformability expressed as a fraction of deformability of fresh, normal, healthy RBCs). In another aspect, deformability is measured as a perfusion rate (nL/s) using a CND and methods of the present disclosure. In another aspect, deformability is determined as a flow rate (nL/s) using a CND and methods of the present disclosure. In another aspect, deformability is measured as a mean number of plugging events using a CND and methods of the present disclosure.

In aspects according to the present disclosure, the deformability is compared to a standard sample. In an aspect, a standard sample is an average value obtained from a normalized population. In another aspect, a standard sample is a range including an average value and the standard deviation obtained from a normalized population.

A normalized population can be a suitable clinical subgroup. In one aspect, a population may be selected based on race, ethnicity, sex and age. In another aspect, a population may be selected based on clinical subgroup such as failure of cardiovascular, respiratory, renal, hematologic, CNS or hepatic organ. In some aspects, a population may be selected based on frequency of transfusion. In an aspect, a clinical group requiring frequent transfusions may provide a population to be used in preparing a standard sample.

According to the present disclosure, a blood sample having an improved or enhanced deformability before or after storage is identifiable by comparison with a normalized population. In an aspect, a normalized population may be an age and sex normalized population. In other aspects, a normalized population may be selected based on weight, glucose tolerance, insulin sensitivity, levels of one or more fatty acids, cholesterol levels and types, etc. In certain aspects, a blood sample may be compared to fresh, healthy, normal RBCs. In some aspects, a blood sample may be compared to a pooled sample of fresh, healthy, normal RBCs. As used herein, normal refers to RBCs obtained from a donor that does not have an underlying blood disease and has blood chemistry values within the normal range. Deformability values from fresh, healthy, normal RBCs may be determined concurrently or established separately as predetermined value.

In other aspects of the present disclosure, the deformability of RBCs before storage can be compared to a predetermined value to determine whether the blood or blood product is suitable for extended storage. In another aspect, the deformability of RBCs after storage can be compared to a predetermined value to determine whether the blood or blood product is suitable for transfusion. A predetermined value can be based upon RBC deformability in comparable samples obtained from the general population or from a select population of humans. For example, a select population may be comprised of apparently healthy individuals. "Apparently healthy," as used herein, means individuals who have not previously had any signs or symptoms indicating the presence of a disease such as metabolic disease, cardiovascular disease, obesity, diabetes, etc.

A predetermined value can take a variety of forms. A predetermined value can be a single cut-off value, such a as a median or mean. A predetermined value can be established based upon comparative groups such as where the level of RBC deformability in one defined group is 80% the level of the corresponding RBC deformability in another defined group. In another aspect, RBC deformability may be 90% of the level of the corresponding RBC deformability in another defined group. In other aspects, RBC deformability may be defined as within one standard deviation of another defined group. Methods to determine statistically significant differences between defined groups are known in the art. A predetermined value can be a range, for example, where the general population is divided equally (or unequally) into groups, or into quadrants, the lowest quadrant being individuals with the lowest levels of RBC deformability, the highest quadrant being subjects with the highest levels of RBC deformability.

In aspects according to the present disclosure, a predetermined value can be derived by determining the respective RBC deformability level in the general population. Alternatively, a predetermined value can be derived by determining the respective RBC deformability level in a select population. For example, a predetermined value may be determined from RBC deformability levels obtained from subject populations in need of transfusion. Accordingly, predetermined values selected may take into account the category in which a subject falls. Appropriate ranges and categories can be selected with no more than routine experimentation by those of ordinary skill in the art.

Predetermined values, such as mean levels, median levels, or "cut-off" levels, may be established by assaying samples of subjects in a general population or a select population. RBC deformability levels determined in a sample test may be compared to a single predetermined value or to a range of predetermined values. In some aspects, the comparison may be to an initial RBC deformability level determined in a subject based on one or more pre-treatment measurements.

In some aspects the RBC deformability may be defined as the ability of RBC to perfuse a microvascular network. In an aspect, CND perfusion may be measured as a bulk rate of flow through the CND to determine RBC deformability. In certain aspects, the bulk rate of flow may be measured at an input channel. In an aspect the bulk rate of flow may be measured at an input microchannel. In another aspect, the bulk rate of flow may be measured at a primary input microchannel. In certain aspects, the bulk rate of flow may be measured at an output channel. In an aspect the bulk rate of flow may be measured at an output microchannel. In another aspect, the bulk rate of flow may be measured at a final output microchannel (e.g., an output channel having the combined CND flow). In other aspects of the present disclosure, CND perfusion may be measured as the sum of the flows through each individual microchannel of a CND. In other aspects of the present disclosure, CND perfusion may be measured as the average of the flows through each individual microchannel of a CND. The present disclosure provides for measurements of RBC deformability that is a flow rate through a CND measured at an inlet port or an outlet port. In an aspect, a measure of RBC deformability may be the number of plugging events of individual microchannels in a CND. In another aspect, the measure of RBC deformability may be the plugging frequency of individual microchannels in a CND. In yet another aspect, the measure of RBC deformability may be an aggregate perfusion index comprising the overall flow rate through a CND and the flow rates in individual microchannels of a CND. In a further aspect, a measure of RBC deformability may be the overall RBC flux through a CND. In an aspect, a measure of RBC deformability may be the RBC flux through individual microchannels of a CND. In an aspect, a measure of RBC deformability may be an aggregate index comprising the RBC flux measured in various channels of a CND.

In accordance with the present disclosure, the reproducibility and sensitivity of CNDs have been demonstrated, and such devices are useful for screening the effect of novel storage conditions, additive solutions, and rejuvenation strategies on rheologic properties of stored RBCs in vitro.

EXAMPLES

Example 1: Capillary Network Device Design

FIGS. 1A-1C show a schematic illustration of the three microfluidic devices according the present disclosure. FIG.

Figure 1E:
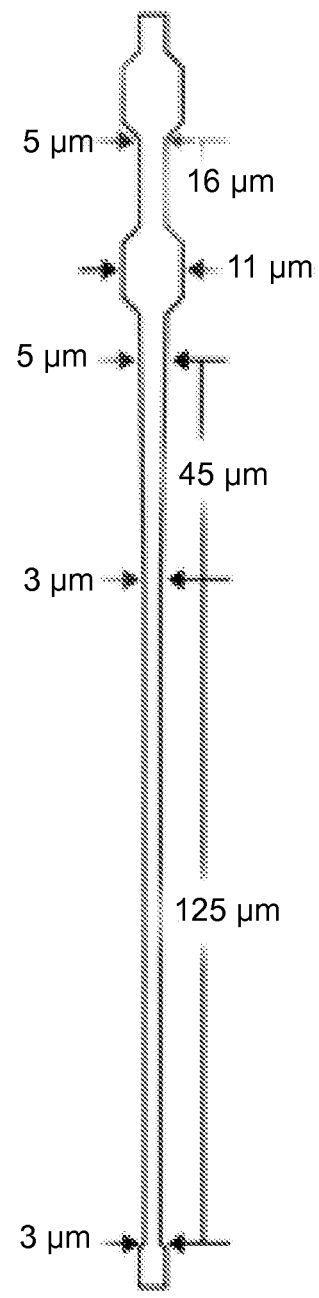

1A shows an aspect of a CND designed to mimic the morphological pattern of a mesenteric microvasculature. CNDs designed to mimic microvasculature may be referred to as an AMVN (Artificial Microvascular Network) device. FIG. 1B shows an alternative Capillary Network Device A (CND-A) having tapered microchannels as illustrated in FIG. 1D. The CND shown in FIG. 1C is another aspect of a Capillary Network Device (CND-B) having a series of repeating constrictions and expansions as illustrated in FIG. 1E.

Example 1A: Branched Artificial Microvascular Network (AMVN) Device

The AMVN device has three identical network units connected by 70 µm inlet microchannels and one common outlet port connected via 70 µm output microchannels. The channels are 5 µm deep. Each network consists of a 70 µm inlet microchannel that bifurcates two to three times to create one or more 5 µm interconnecting microchannels. The bifurcated channels then converge to microchannels of 13 µm and 23 µm before converging to the 70 µm output microchannel (FIG. 1A inset).

Example 1B: Capillary Network Device A (CND-A) and B (CND-B)

CND-A illustrated in FIG. 1B and CND-B illustrated in FIG. 1C are designed to be identical except for the shape of their microchannel elements (the microchannels located in the center of the networks). Each device consists of two identical network units with two independent inlet ports and one common outlet port. Each network unit consists of a 70 µm inlet microchannel connecting the inlet port to a parallel array of 32 microchannel via a series of bifurcating junctions; each capillary array drains through a series of junctions to converge into a single 70 µm outlet microchannel. The microchannel arrays of FIGS. 1B and 1C are depicted in FIGS. 1D and 1E, respectively. In FIG. 1B, the tapered microchannels of CND-A comprise a 330 µm long, 5 µm wide straight portion followed by a 45 µm long portion gradually tapering to a 3 µm wide section that further extends to a length of 125 µm on the output side (FIG. 1D). In FIG. 1C, the microchannels of CND-B comprise a 330 µm long portion with a series of 10 repeating constrictions (5 µm) and expansions (11 µm), followed by a 45 µm long portion gradually tapering to a 3 µm wide section that further extends to a length of 125 µm on the output side (FIG. 1E). The depth of all the channels is 5 µm throughout. The topology of the networks in CND-A and CND-B is matched, making the nominal fluidic resistance in both devices comparable. Both CND-A and CND-B test the ability of individual RBCs in mass succession to squeeze through the tiny microchannel of the network (with diameters similar to those found in the spleen). The configuration of CND-A and CND-B allow for the determination of the ability of individual RBCs in a bulk fluid to deform. Thus, small subpopulations of RBCs may be identified that affect the overall flow properties of the bulk sample.

Example 2: Capillary Network Device Fabrication

Figure 2E:
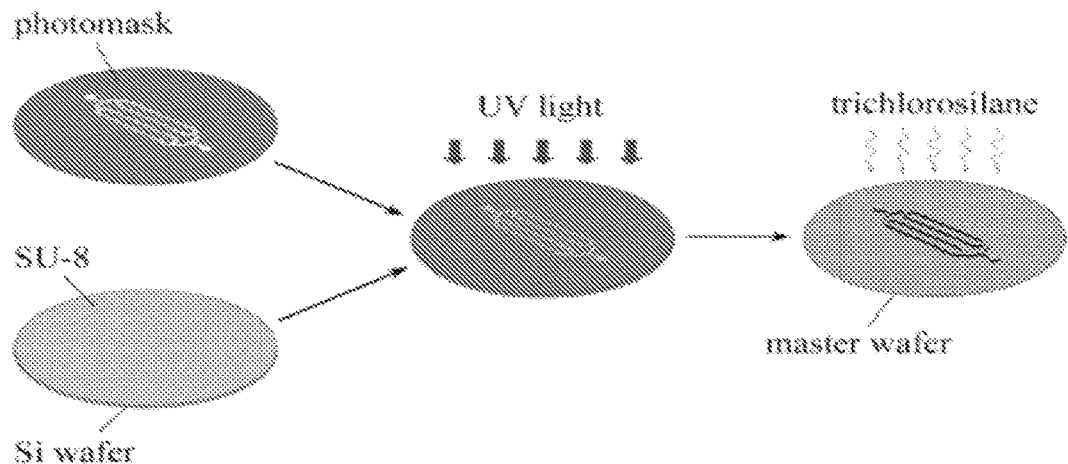

In certain aspects, FIGS. 2A-2G illustrate exemplary CND fabrication. In this regard, conventional photolithography may be utilized to create a 5-mm-high bas-relief of the channels of the device on a silicon wafer. CNDs may be fabricated using general soft lithography techniques (Xia Y, Whitesides G M. Soft lithography. *Angew Chem Int Ed Engl* 1998; 37:550-75; Sia S K, Whitesides G M. Microfluidic devices fabricated in poly(dimethylsiloxane) for biological studies. *Electrophoresis* 2003; 24:3563-76). Small droplets of photoresist are placed onto the outlines of three inlet ports and an outlet port to form dome-shaped three-dimensional structures of the inlet and outlet ports (FIG. 2A). The droplets create a smooth, gradual transition between the macroscopic access openings of the ports and the shallow 5-mm-deep microchannels of the device (FIGS. 2C and 2D). The gradual tapering of the inlet wells (e.g., port) into the adjoined microchannels minimize the "screening" of RBCs at the inlet port based on their shape and deformability (a phenomenon previously observed for similar devices with a sharp transition between a macroscopic inlet port and shallow microchannels in the context of white blood cell separation) and, thus, reduce the possible bias of the RBC population in the samples. The impressions left by the droplets in the PDMS replica molds makes the inlet ports and the outlet ports easily visible and enables more accurate centering of the biopsy punches to cut the access holes (the features have a slightly larger diameter than the punches). The use of droplets reduces the variability associated with this manual step and ultimately enables fabrication of a reproducible interface between the inlet ports and the microfluidic channels in every device. The outlet port of an AMVN assembled device is connected to the reservoir of the water column via an L-connector and a length of plastic tubing. The L-connector is inserted into the opening of the outlet port flush with the top surface of the device to minimize the possible deformation of the outlet port during the experiment and to improve reproducibility (FIG. 2B).

The process to create a bas-relief pattern of the CND on a master wafer, (PWM32-PS-R790, Headway Research, Inc., Garland, Tex.) is illustrated in FIG. 2E. A 5-µm layer of SU-8-negative photoresist is spin-coated (SU-8 2005, MicroChem Corp., Newton, Mass.) onto a silicon wafer (University Wafer, South Boston, Mass.) and the wafer is exposed to near-UV light through a high-resolution chrome photomask (Photo Sciences, Inc., Torrance, Calif.) using a mask aligner (ETI/6/350/NUV/DCCD/M, Evergreen Technology, Inc., San Jose, Calif.). (Shevkoplyas S S, Gifford S C, Yoshida T, Bitensky M W. Prototype of an in vitro model of the microcirculation. *Microvasc Res* 2003; 65:132-6; Shevkoplyas S S, Yoshida T, Gifford S C, Bitensky M W. Direct measurement of the impact of impaired erythrocyte deformability on microvascular network perfusion in a microfluidic device. *Lab Chip* 2006; 6:914-20.) After development, the patterned wafer is treated with (tridecafluoro-1,1,2,2-tetrahydrooctyl)trichlorosilane (CAS #78560-45-9, Gelest, Inc., Morrisville, Pa.) in a vacuum chamber overnight.

To fabricate the large three-dimensional domed structures of the inlet port and the outlet port, the patterned wafer is set on a digital hot plate (Torrey Pines Scientific, Inc., Carlsbad, Calif.) and small droplets of SU-8 2007 photoresist (of sufficient volume to produce a hemisphere) are carefully placed onto the circular regions predefined as the inlet ports (17 uL) and the outlet ports (1.8 uL) (FIG. 2A). (Hulme S E, Shevkoplyas S S, McGuigan A P, Apfeld J, Fontana W, Whitesides G M. Lifespan-on-a-chip: microfluidic chambers for performing lifelong observation of C. elegans. *Lab Chip* 2010; 10:589-97; Forouzan O, Burns J M, Robichaux J L, Murfee W L, Shevkoplyas S S. Passive recruitment of circulating leukocytes into capillary sprouts from existing capillaries in a microfluidic system. *Lab Chip* 2011; 11:1924-32.) The wafers are coated with tridecafluoro (1,1, 2,2 tetrahydrooctyl) trichlorosilane to make the surface hydrophobic to create large 3D domed structures on the inlet ports and outlet ports of the network devices on the master wafer. The domed structures are fabricated to eliminate or reduce a selective screening of non-deformable cells or large macroaggregates from entering the microscopic channels of the device by creating a smooth, gradual transition between the macroscopic inlet port and microscopic channels. The wafer is then soft-baked at 85° C. overnight, exposed to near-UV light (two times for 6 min), and postbaked at 95° C. for approximately 5 hours. A relatively slow heating and cooling ramp is used (180° C./hr) to minimize the possibility that the domed inlet port and outlet port structures peel off or crack.

Figure 2F:
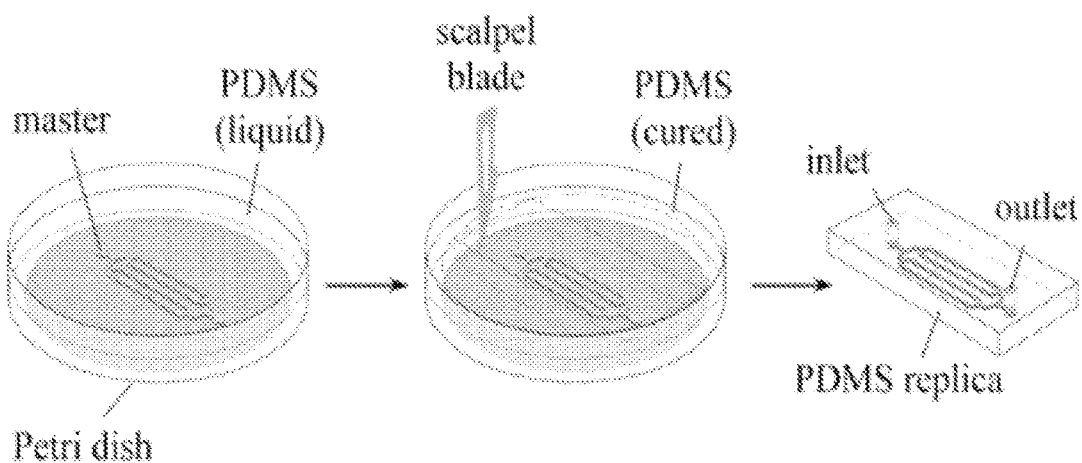
Figure 2G:
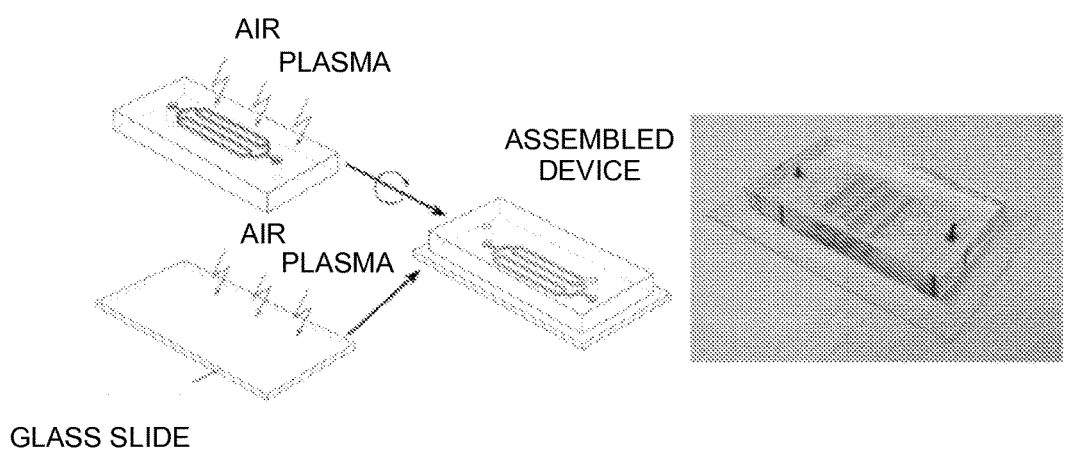

The master wafer is treated with (tridecafluoro-1,1,2,2-tetrahydrooctyl)trichlorosilane for the second time after completing the inlet and outlet ports. The master wafer is treated to mold many replicas of the CND in polydimethylsiloxane (PDMS; Sylgard 184, Dow Corning Corp., Midland, Mich.) (FIG. 2F). Access holes are created in the PDMS replicas using biopsy punches (Acuderm, Inc., Fort Lauderdale, Fla.)—4 mm for the inlet ports and 2 mm for the outlet port. To assemble a CND, the patterned surface of a PDMS replica and a glass slide (VWR, West Chester, Pa.) spin-coated with a thin layer of PDMS (approx. 50 mm) is exposed to air plasma (120 sec, PDC-3xG, Harrick Plasma, Ithaca, N.Y.) and the two parts are sealed together (FIG. 2G). Assembled devices are filled with a 1% solution of mPEG-silane (Laysan Bio, Inc., Arab, Ala.) in GASP buffer (9 mmol/L $Na_2HPO_4$, 1.3 mmol/L $NaH_2PO_4$, 140 mmol/L NaCl, 5.5 mmol/L glucose, 1% bovine serum albumin (BSA), 290 mmol/kg, pH 7.4) and incubated for at least 6 hours at room temperature to prevent adhesion of blood cells to the walls of the microchannels.

Example 3: Measurement of Network and Capillary Flow Rates

To perform an experiment, a CND is secured on a mechanical stage of an inverted microscope (IX71, Olympus America, Inc., Center Valley, Pa.). The inverted microscope is equipped with a high-speed CMOS digital camera (MC1362, Mikrotron GmbH, Unterschleissheim, Germany) connected to a desktop computer (HP Pavilion Elite e9180f, Core i7 920/2.66 GHz/9 GB/1 TB, Hewlett-Packard Company, Palo Alto, Calif.) using a frame grabber (Camera Link, PIXCI E4, EPIX, Inc., Buffalo Grove, Ill.). A narrow band-pass blue filter (394±50 nm, B-390, Hoya Corp. USA, Fremont, Calif.) is used to improve image contrast (RBCs appear dark in blue light). A custom software application (Microsoft Visual Studio 2008, Microsoft Corp., Redmond, Wash.) using a C++ function library provided with the frame grabber (XCLIB, EPIX, Inc.) may be used to control the variables and timing of image acquisition during the experiment. Images are recorded on the hard drive of the desktop computer and then analyzed off-line using custom software (written in MATLAB R2009b, The Math Works, Inc., Natick, Mass.).

A simple water column assembly is used to provide the hydrostatic pressure difference between the inlet ports and the outlet ports necessary to drive the samples through the device. The water column may include a large reservoir (a plunger-less 30-mL syringe, BD, Franklin Lakes, N.J.) attached to a linear motion stage (Series A40 UniSlides, Velmex, Inc., Bloomfield, N.Y.) mounted vertically and a length of flexible tubing (Tygon R-3603, VWR) connecting the water column reservoir to the outlet port of the device via an elbow reduction tube fitting (L420/410-6, Value Plastics, Fort Collins, Colo.).

To perform a measurement of CND network and capillary for each of the three RBC samples, the outlet port of the device is connected to the water column, the device is placed onto the stage of the microscope securely, and the device is flushed with fresh saline solution.

To load the samples into the device, equal volumes (25 uL) of each of the samples are placed in their corresponding inlet ports and the reservoir of the water column is lowered to establish a driving pressure of approximately 10 $cmH_2O$. The samples are then allowed to fill the CND until the RBCs reach the outlet port, at which point the driving pressure is zeroed by adjusting the height of the water column reservoir until RBCs stop moving; this level of the water column is then marked as $\Delta P=0$ $cmH_2O$.

Figure 3:
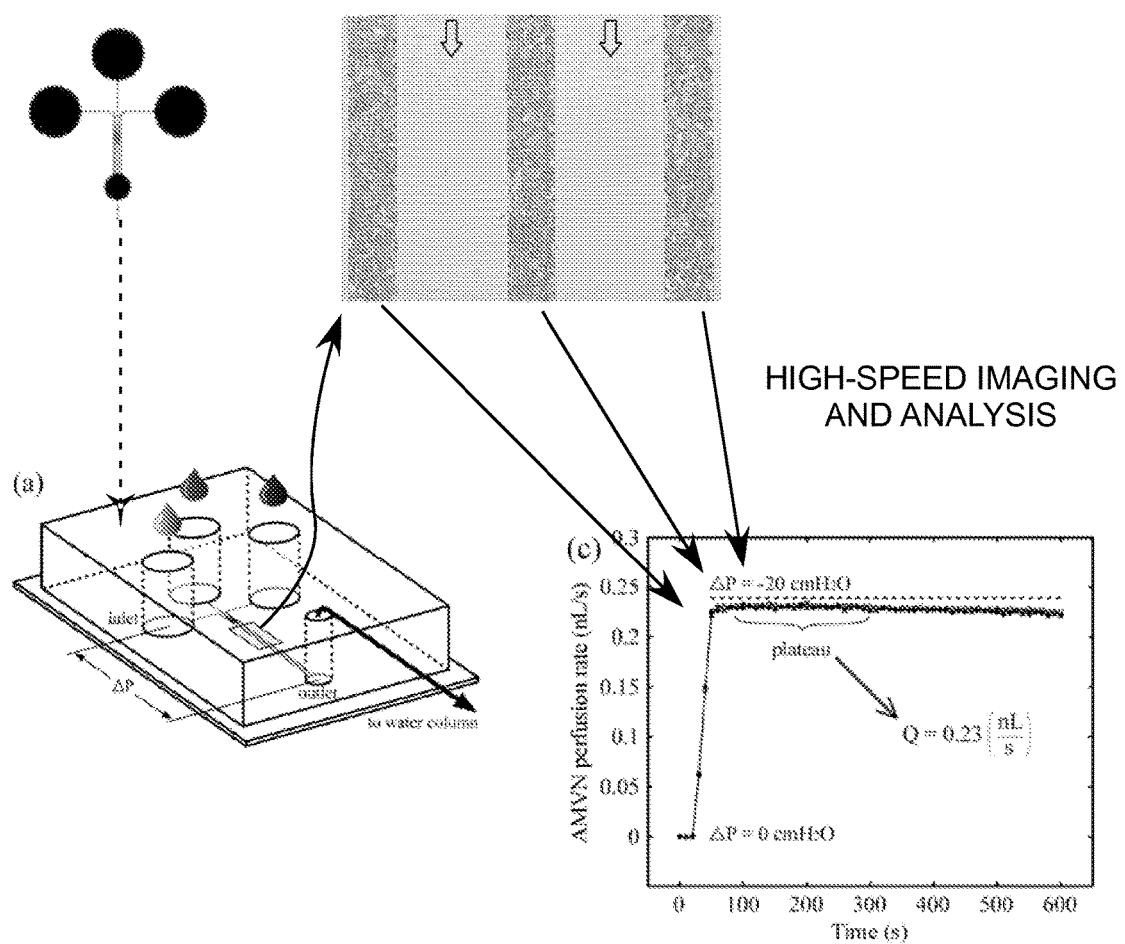
FIG. 3 illustrates methods of using an exemplary Capillary Network Device (CND) to measure perfusion according to the disclosure.

The field of view of the image capture camera is aligned to the venules of the AMVN capillary network in the device and image capture is initiated in short sequences of images (10 frames at 100 fps with 3-msec exposure and global shutter) every 10 seconds for the duration of the experiment (up to 10 min) (FIG. 3). The first three measurements are taken at a driving pressure of 0 $cmH_2O$, and then the driving pressure differential is increased to a constant −20 $cmH_2O$. The recorded image sequences are analyzed off-line to determine the mean velocity of RBCs in each of the venules of the device.

Example 4: Quality Control and Reproducibility

A visual 10-point inspection for fabrication defects in every network device is performed three times—before loading a sample, immediately after loading a sample and upon completion of a measurement. Devices that do not pass this quality control (QC) measure are discarded (<10%). The overall reproducibility of network flow rate measurements and estimate of the percentage of variation between the channels within a single device is about 1%, and between the channels of different devices is about 2% (FIG. 4).

Figure 4A:
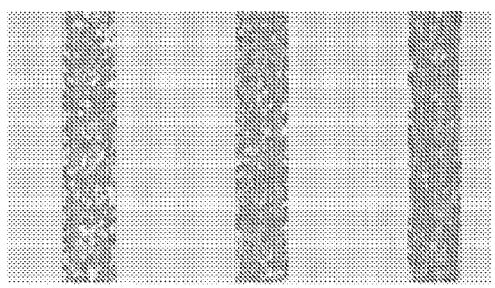
FIGS. 4A-4F illustrate analysis of quality control and reproducibility of CNDs according to the disclosure.
Figure 4B:
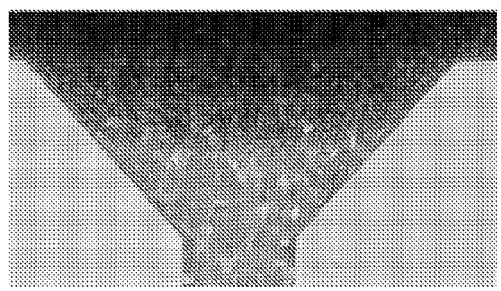
Figure 4C:
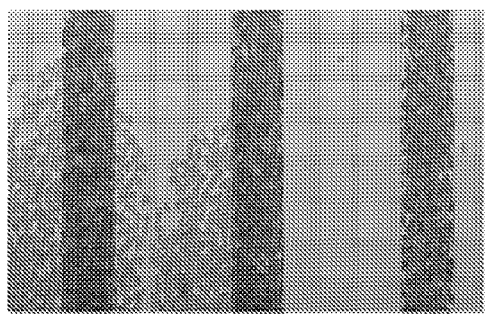
Figure 4D:
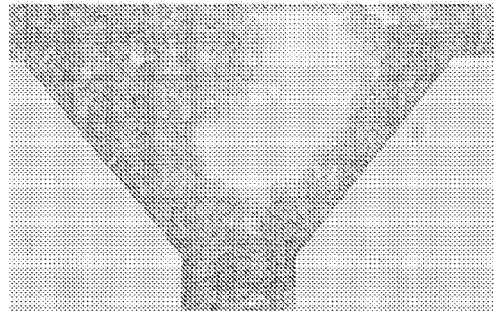
Figure 4E:
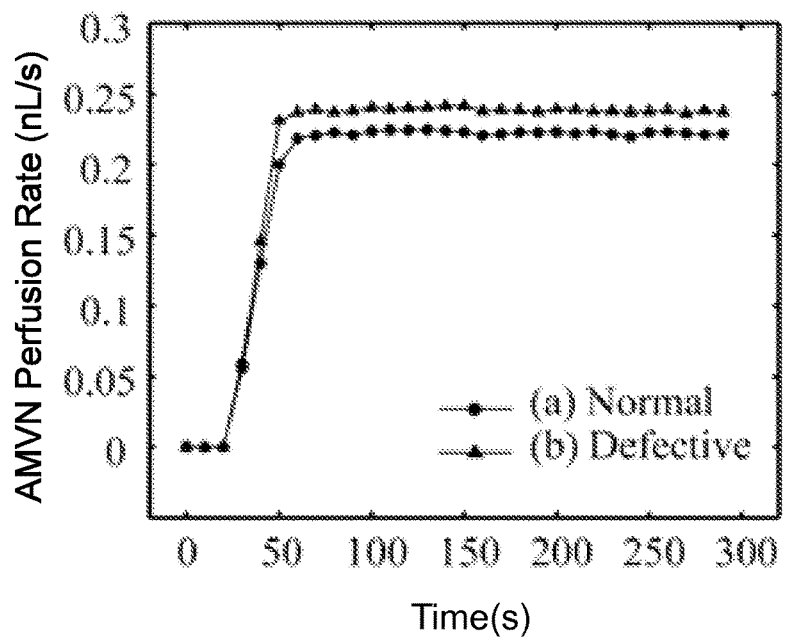
Figure 4F:
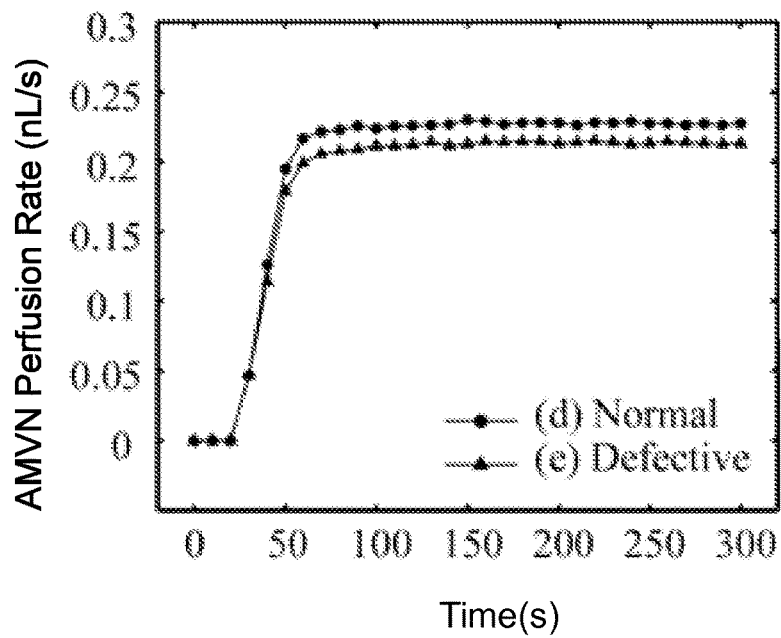

The bulk flow rates of the RBCs through the networks in all three devices is performed as described above. The recorded image sequences are analyzed off-line using custom software written in MATLAB to determine a mean flow rate of RBCs in each venule of each network units of the device. For the venules, the centerline flow rates of the RBCs are determined by cross-correlating two images in sequence, determining the shift in pixels between the two images, and averaging the pixel shift for each time interval. A time-dependent trace of RBC flow rates (in nL/s) is determined using this process (FIGS. 4C and 4F). At a differential pressure of 20 $cmH_2O$, the flow rates for the region of the time trace that is not affected by sedimentation is averaged and compared across samples (for details refer to Burns J M, Yang X, Forouzan O, Sosa J M, Shevkoplyas S S. Artificial microvascular network: a new tool for measuring rheologic properties of stored red blood cells. *Transfusion* 2011).

The capillary flow rates of the RBCs in Device A and Device B are measured immediately following the measurement of the bulk flow rate. The field of view of the camera is aligned to the 32 microchannels of a single network unit in the device under 20× magnification and a single sequence of images (500 frames at 100 fps with 1.994 ms exposure) is acquired for 5 seconds at a differential pressure of 20 $cmH_2O$. These recorded image sequences are analyzed off-line using custom software written in MATLAB to determine a time-dependent trace of RBC flow rates (in nL/s) in each capillary of a single network unit of the device (similar to the software written for determining flow rates in the venules).

For individual microchannels, the flow rates of the RBCs are determined using the same method for a sequence of images (1000 frames at 100 fps for 10 sec); however, pixel shift is not averaged but used as a time-dependent trace of RBC flow in each of the individual microchannels.

Overall network flow rate is directly dependent on the flow rates in individual microchannels. Individual, non-deformable RBCs damaged in hypothermic storage may plug a significant number of the microchannels along the length where they narrowed to 3 µm in width, as depicted in FIGS. 1D and 1E. Plugging of these microchannels and increased fluidic resistance (caused by cell-cell and cell-wall interactions) cause significant changes in the flow rates of the other microchannels, thereby causing "oscillatory" traces of flow rates, and reduces the overall bulk flow of the RBCs through the network. In FIGS. 5B, 5F, and 5H, transient plugging of the microchannels of the arrays of an AMVN device of FIG. 1B (see, also, FIG. 5F), and FIG. 1C (see, also, FIG. 5H), by non-deformable RBCs damaged in hypothermic storage are illustrated.

Example 5: Data Analysis

Bulk flow rates for each RBC sample are measured three times in three to four AMVN, and twice in CND-A device and CND-B devices. Capillary flow rates are measured in a single network of 32 microchannels in a CND-A or CND-B and values are reported as means with p-values after excluding for defective delivery of samples and microfluidic devices. Eight to 13 donor units ($n_{donor}$) are used with the AMVN device and 4 to 8 are used with CND-A or CND-B. P-values are determined by using paired two-tailed, unequal variance t-tests of statistical significance.

Example 6: Collection and Preparation of Red Blood Cell (RBC) Samples

Human whole blood is collected by venipuncture from healthy consenting volunteers into 4-mL VACUTAINER® tubes (K2EDTA, BD). Whole blood is transferred from the VACUTAINER® tube into a 50-mL conical tube, centrifuged at 600 ¥ g for 15 minutes at room temperature (ALLEGRA® X-15R, Beckman Coulter, Fullerton, Calif.) to remove blood plasma. The RBC pellet is then resuspended in approximately 50 mL of saline solution (0.9% NaCl, 295 mmol/kg, pH 7.4) and passed through a high-efficiency leukoreduction filter (PURECELL® NEO, Pall Corp., Port Washington, N.Y.). The leukoreduced suspension of fresh RBCs is left on the counter for 30 minutes and then centrifuged again at 600×g for 15 minutes to remove the washing medium (the saline solution). Washed RBCs are resuspended in saline at the target Hct of 40%. The original whole blood samples may have the white blood cell (WBC) count of 5.8±0.9 ($10^9$/L) and platelet (PLT) count of 219±79 ($10^9$/L). The leukoreduction protocol used to prepare the fresh RBC samples may reduce WBC and PLT counts below the detection limit of the hematology analyzer (MEDONIC™ M-Series, Boule Medical AB, Stockholm, Sweden).

Five units of RBCs (CPD>AS1; leukoreduced; blood groups O+, A+, and AB+; Hct, 57±4%; mean cell volume, 95±3 fL; mean corpuscular hemoglobin (Hb) concentration, 30.7±0.6 g/dL) from a local blood bank (The Blood Center, New Orleans, La.) may be collected and stored in a blood bank refrigerator (Jewett BBR6-1B18, Thermo Fisher Scientific, Asheville, N.C.). To prepare stored RBC samples from an RBC unit, the blood bag may be removed from the refrigerator, placed on a rocking platform (Model 100, VWR) for 5 minutes, the contents mixed by gently massaging and flipping the bag (approx. 1 min), and then a sampling site coupler (Fenwal, Inc., Lake Zurich, Ill.) may be inserted into one of the sampling ports of the blood bag using aseptic technique.

Sixty mL of RBCs may be extracted from the bag into a sterile syringe (BD), and then 4 mL may be used to prepare samples and the rest (approx. 56 mL) centrifuged at 600×g for 15 minutes to obtain the storage medium needed in the sample preparation (described below). The remaining 4 mL may be split into two 2-mL samples and placed into a 15-mL conical tube. The samples may be centrifuged at 600×g for 15 minutes to remove the storage medium from the cells. For one sample, the RBC pellet is then resuspended in 13 mL of their own storage medium (obtained as described above). For the other sample, the RBC pellet is resuspended in 13 mL of saline. Both samples are gently mixed, allowed to incubate at room temperature for 30 minutes, and then centrifuged again at 600×g for 15 minutes to remove the washing medium. Finally, pelleted RBCs of both samples are resuspended at a Hct of 40% in their respective media (storage medium for one and normal sterile saline for the other). All three RBC samples are kept on a tube rotator (Barnstead Thermolyne, Dubuque, Iowa) to maintain uniformity of Hct. Blood cell counts and Hct concentrations are determined using a hematology analyzer (MEDONIC™ M-Series, Boule Medical AB, Stockholm, Sweden).

Example 7: Measurements of Protein Concentration and Viscosity of Suspending Media and of RBC Aggregation To determine the concentration of protein and viscosity of the suspending media, all samples (e.g., fresh RBCs washed and suspended in saline, stored RBCs washed and suspended in saline, and stored RBCs washed and suspended in storage medium) are prepared following the protocol described above, but in 3× larger volume. After the Hct concentrations of the samples are adjusted to 40%, a volume of each sample is used for measuring RBC aggregation and the rest is centrifuged at 800×g for 5 minutes to separate the cells from the suspending medium. The effluent medium is then centrifuged again at 6000×g for 5 minutes and used for measuring the concentration of protein and viscosity.

Total protein concentration (n=10) and Hb concentration (n=10) are measured spectrophotometrically (660/540 nm, SPECTRAMAX® 190 absorbance microplate reader, Molecular Devices, Inc., Sunnyvale, Calif.) following the manufacturer's instructions for a 660-nm protein assay (Pierce, Fisher Scientific, Inc., Pittsburgh, Pa.) and Drabkin's reagent (RICCA Chemical Company, Arlington, Tex.), respectively. The relationship between absorbance and the concentration of protein is calibrated using prediluted standards: BSA (Fisher Scientific, Inc.) and Hb (Pointe Scientific, Inc., Canton, Mich.) in the range from 0 to 2000 mg/mL.

Viscosity of the suspending medium for each sample is measured with a cone and plate viscometer (DV-II+ Pro, Cone CPE-40, Brookfield, Middleboro, Mass.) using 0.5 mL volume of the suspending medium for each measurement (n=2-3). The viscometer is calibrated using standard values of viscosity for deionized water. (Haynes W M, Lide D R, editors. CRC Handbook of Chemistry and Physics. 91st ed. Boca Raton (Fla.): CRC Press; 2010. p. 2010-1.)

Aggregation of the samples is measured using a microfluidic ektacytometer (Rheoscan-D300, Rheo Meditech, Inc., Seoul, Republic of Korea) based on laser transmission rheometry. Each cartridge (Rheoscan-D-test kit RSD-K01, Rheo Meditech, Inc.) is filled with 0.5 mL of sample for each measurement (n=3-5), and the cartridge is placed into the automated stage of the ektacytometer to measure the transient transmitted light intensity. Aggregation results are reported in terms of critical shear stress where the "critical shear stress" is defined as the minimum shear stress necessary to disperse RBC aggregates. (Shin S, Nam J H, Hou J X, Suh J S. A transient, microfluidic approach to the investigation of erythrocyte aggregation: the threshold shear-stress for erythrocyte disaggregation. *Clin Hemorheol Microcirc* 2009; 42:117-25.)

Example 8: Preparation of Red Blood Cell Samples

Stored leukoreduced RBC samples are prepared as previously described (L J Dumont1, Z M Szczepiorkowski, A H Siegel, L Herschel, K E Calcagni, S L Waters, T Yoshida. "Performance of Anaerobic Stored Red Blood Cells Prepared Using a Prototype O2 & CO2 Depletion and Storage System," Transfusion 2011; 51(suppl):77A). Paired RBC units are stored in conventional (aerobic) and anaerobic conditions (deoxygenated and stored in oxygen-impermeable bags) in AS-3 for 63 days. Two RBC units are obtained from whole blood collected, on separate occasions, from each donor and used for obtaining measurements in the AVMN device ($n_{donor}$=13, $n_{RBCunit}$=26), Device A and Device B ($n_{donor}$=8, $n_{RBCunit}$=16); one arm unit is stored aerobically and the other anaerobically. The aerobic RBC unit (control) is collected, processed, and stored in AS-3 (Nutricell, Pall Medical) for 9 weeks at 1-6° C. according to standard procedures. The anaerobic RBC unit (test) is prepared by passive flow through a device with a special hollow fiber filter with a sorbent material to remove $O_2$ and $CO_2$ from the RBCs followed by transfer into an oxygen-impermeable bag (HASP, New Health Sciences, Inc) containing the same storage solution (AS-3) as the conventional RBC unit. Each RBC sample (2 mL vial) is kept either on ice or a chemical cooling bag to maintain a temperature between 0-10° C. within a Styrofoam container. Upon arrival, each sample was placed in a blood bank refrigerator at 1-6° C. until use. On the day of an experiment, the sample is taken out of the blood bank and gently mixed. Hematological parameters (including hematocrit) of the RBC sample are taken via a hematology analyzer (Medonic M-Series, Boule Medical AB, Stockholm, Sweden). The mean hematocrit of the conventionally stored RBC units is 44% and for the anaerobically stored RBC units is 37%. The hematocrit of the sample is adjusted to 40% either by adding normal 0.9% saline solution (pH=7.4) or by removing the supernatant of the sample (storage solution AS-3) via gentle centrifugation (800×g for 5 min). The volume of saline added or supernatant removed in this study does not significantly affect (<1%) the measurements of bulk flow perfusion rates (in separate experiments). After the adjustment of haematocrit, the sample is placed on a tube rotator (Barnstead Thermolyne, Dubuque, Iowa) for the duration of the experiment (<6 hrs). Both units are sampled and measurements of RBC deformability are conducted on Days 2, 21, 42, and 63.

Example 9: Measurement of the AVMN Perfusion

Figure 5A:
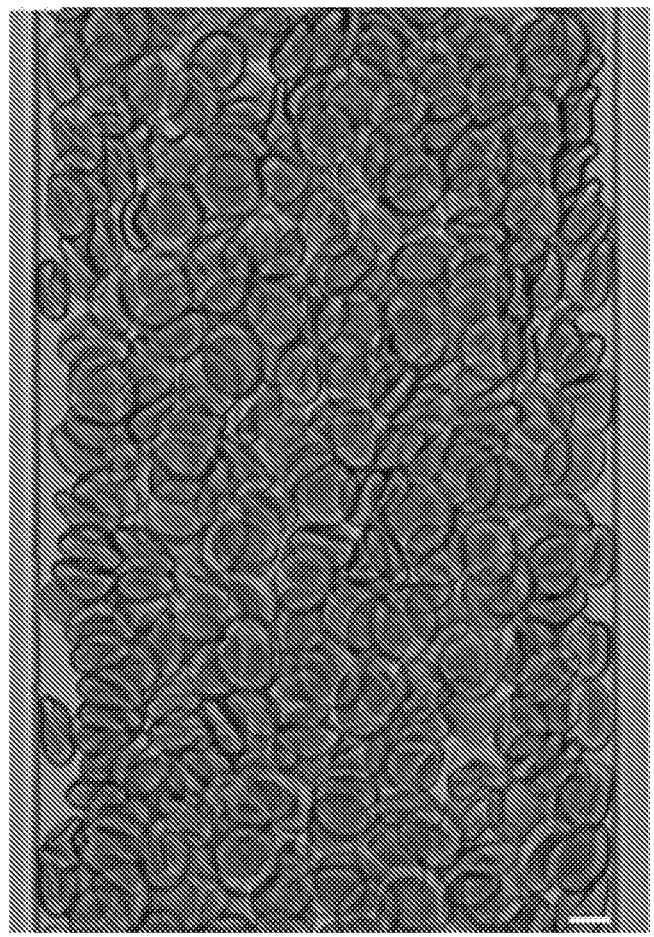
FIGS. 5A-5F illustrate exemplary RBC deformations and transient plugging in Capillary Network Devices (CNDs) in accordance with exemplary aspects of the disclosure.
Figure 5B:
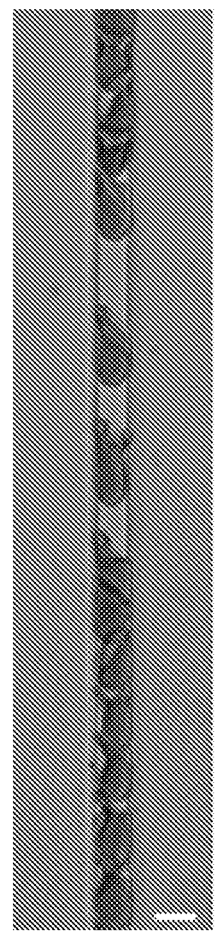
Figure 5C:
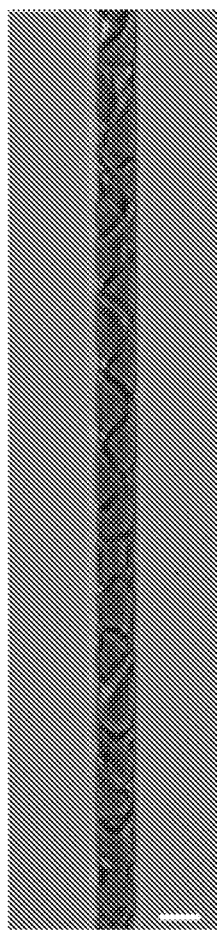
Figure 5D:
Figure 5E:
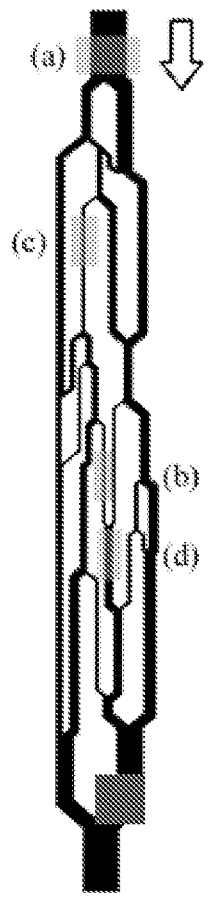
Figure 5F:
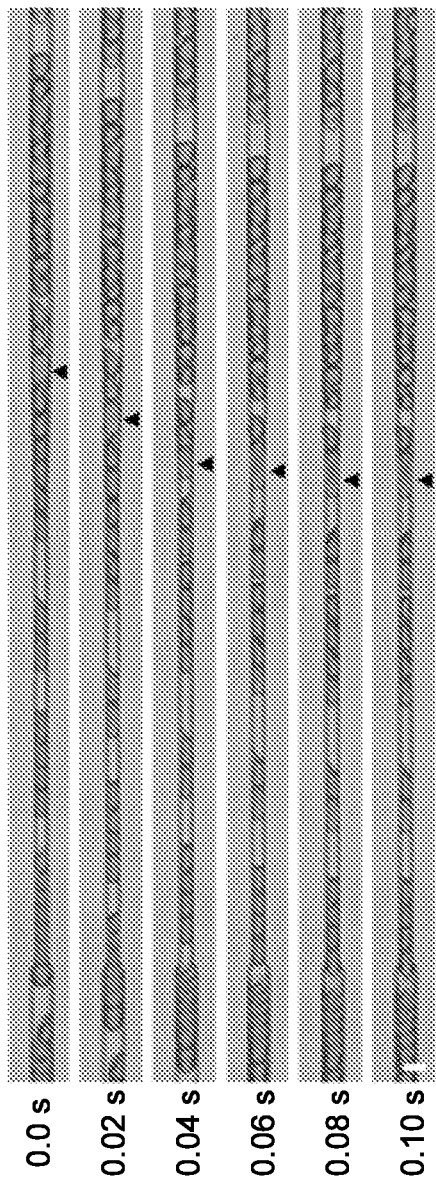
Figure 5G:
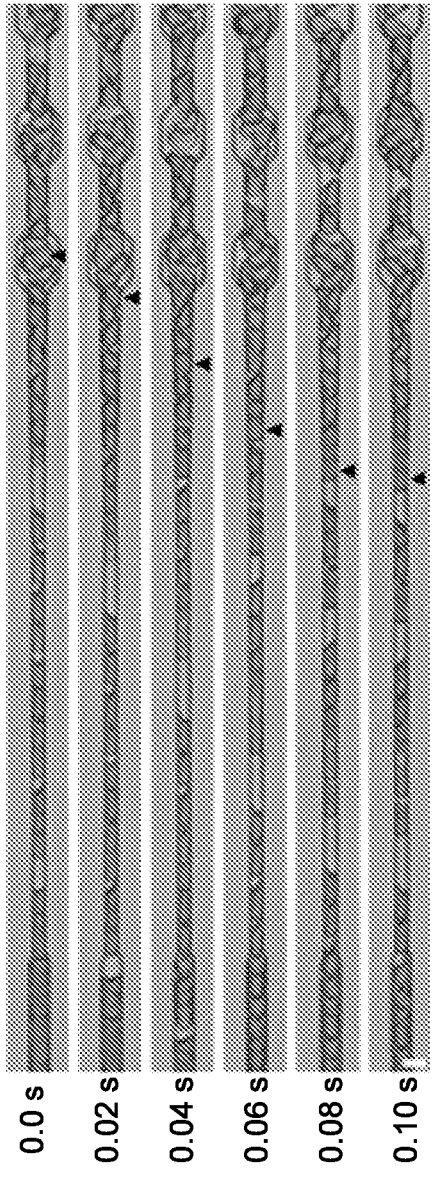

FIGS. 5A-5D show representative images of the types of deformations experienced by RBCs in the microchannels of the AMVN perfused by a 40% Hct suspension. In larger vessels (arteriole and venule), high shear stress experienced by the cells near the walls of the vessels is the primary source of RBC deformations; the cells in the middle of the stream (where the shear stress is relatively low) deform much less (FIG. 5A). RBC tumbling induced by shear (most evident in our system near the sidewalls) at physiologically high Hct concentrations results in numerous cell-cell collisions and a wide variety of deformations of the biconcave disk shape of RBCs observed in static conditions (FIG. 5A). To enter the 5-μm microchannels (the narrowest microchannels of the network), RBCs undergo folding deformation and assume the characteristic bullet-like shape, which they retain while traversing the vessels (FIG. 5B). At higher Hct concentrations, the deformed RBCs have the ability to pack in a dense staggered arrangement and still continue to flow through the capillary (FIG. 5C). RBCs gradually recover from the folding deformation upon exiting the narrow microchannels and continue to change their shape as they collide with other cells (FIG. 5D). The rheologic response by RBCs to the deforming forces in the vessels of the network contributes to the effective viscosity of the suspension and changes the fluidic resistance of the network and (under the condition of a constant pressure difference ΔP applied to the inlet and the outlet of the network) could be monitored by measuring the overall flow rate through the network (AMVN perfusion rate). The measurement of the AMVN perfusion rate can be done either in the inlet microchannel (arteriole) or in the outlet microchannel (venule).

Example 10: Capillary Flow Rates of Stored RBCs

The trace of RBC suspension flow rates in each of the 32 microchannels comprising a single network in Device A and Device B is determined. Capillary flow traces of both RBC samples exhibits a characteristic pattern over the 63 days of cold storage, in which transient plugging of the microchannels occurs more frequently over the duration of storage. FIG. 5F demonstrates the transient, and occasionally permanent, plugging of the pipette-like microchannels by poorly deformable RBCs from Day 42 of conventionally stored samples in CND-A (FIG. 5E). FIG. 5H demonstrates the transient, and occasionally permanent, plugging of the pipette-like microchannels by poorly deformable RBCs from Day 42 of conventionally stored samples in CND-B (FIG. 5G).

Example 11: Effects of Storage on Perfusion

To test the sensitivity of the AMVN perfusion measurements to changes in RBC properties occurring in storage, 5 RBC units (leukoreduced, AS-1) are tested. RBC units arrived from the blood bank in thermally insulated containers (filled with ice and water mixture) 2 to 3 days before expiration and are placed in a blood bank refrigerator upon arrival to maintain the appropriate storage conditions. Each unit is tested 1 day before the scheduled expiration of the unit, e.g., on Day 41 of its storage. On the day of an experiment, a sample of fresh RBCs to be used as a calibration control is prepared from blood from a healthy consenting volunteer.

Figure 6A:
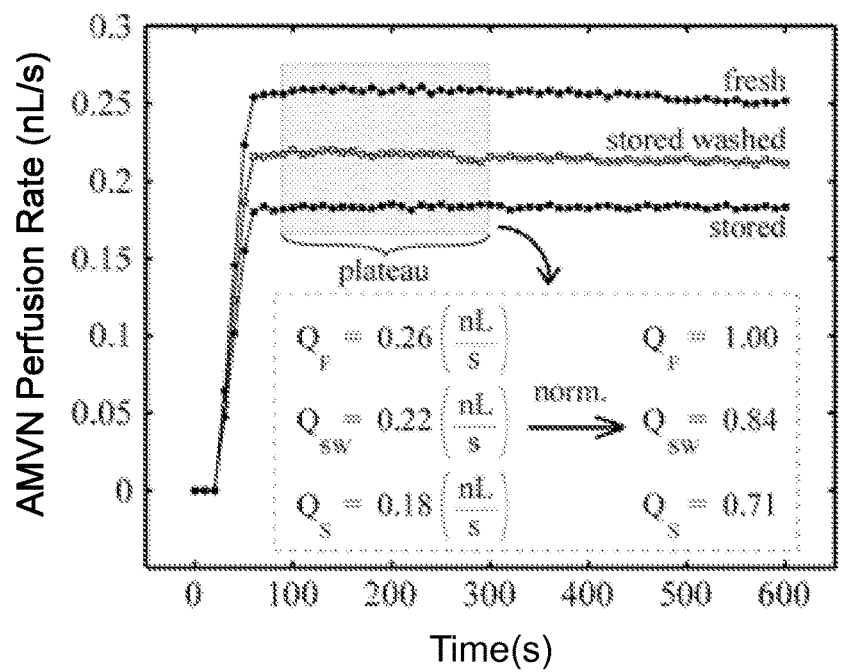
FIGS. 6A-6B illustrate results of perfusion analysis using an exemplary CND of the present disclosure for fresh, stored and stored washed blood according to the disclosure.

FIG. 6 illustrates the approach to measuring the AMVN perfusion in accordance with the present disclosure for three blood samples simultaneously. A water column is used to establish the driving pressure difference between the inlet ports and the outlet port of the AMVN device, as described above. The evolution of these perfusion rate values in time followed a characteristic trend. During the initial stage of an experiment (AP=0 cmH$_2$O), the AMVN perfusion remained zero and then gradually increased as AP decreased from 0 to −20 cmH$_2$O. As AP remained at a constant −20 cmH$_2$O, the perfusion rate equilibrated and reached a plateau that lasted from 80 to 300 seconds of an experiment. The steady decline of the perfusion rate observed thereafter is attributed to the progressive rise in Hct of the samples due to the sedimentation of RBCs in the inlet ports. The mean AMVN perfusion rate (Q) for each sample is calculated by averaging the values of the perfusion rate measured every 10 seconds between the 80 and 300 seconds of the experiment (FIG. 6). The same plateau region of the trace is used to calculate the average AMVN perfusion rate for all samples and devices, for consistency.

Figure 6B:
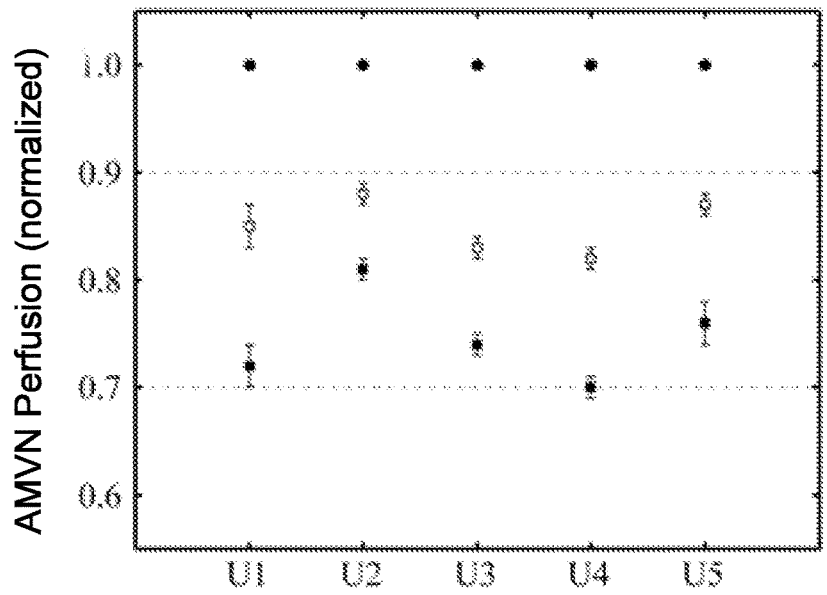

For each RBC unit, three different samples are prepared: 1) stored RBCs washed and suspended in their own storage medium AS-1 (stored), 2) stored RBCs washed and suspended in saline (stored washed), and 3) fresh RBCs washed and suspended in saline (fresh). Samples 1 (stored) and 3 (fresh) are prepared through the same "washing" procedure as Sample 2 (stored washed), except Sample 1 is "washed" in its own storage medium and Sample 3 is also leukoreduced in the process. The Hct of all three RBC suspensions are adjusted to 40%. The average AMVN perfusion rate (Q) for all three samples are determined simultaneously (FIG. 6A) and the measurement is repeated five times (using a new AMVN device every time) for each RBC unit (FIG. 6B).

The AMVN perfusion rate for stored RBCs washed and resuspended in their own medium is 19% to 30% lower than for fresh RBCs depending on the unit (26±4% lower overall). Washing of stored RBCs in saline improves their ability to perfuse the AMVN by a mean of 41±6% for all units (the perfusion rate for washed cells is still 15±2% less than for fresh RBCs).

The results of the measurements of total protein concentration, of Hb concentration and viscosity of the suspending media, and of RBC aggregation for the three samples are shown in Table 1. The measured differences in the AMVN perfusion rate between the samples (FIG. 6) cannot be explained by the differences in concentration of protein present in the suspending media (through the effect of plasma proteins on viscosity of the medium and/or RBC aggregation), rather than RBC deformability.

The suspending medium of the sample of fresh RBCs washed and suspended in saline has the lowest total protein concentration (1.04±0.06 g/L), followed by the sample of stored RBCs washed and suspended in saline (2.85±0.53 g/L) and the sample of stored RBCs washed and suspended in storage medium (9.95±0.10 g/L). (For reference, fresh blood plasma had a total protein concentration of 68.2±3.3 g/L, which is within the normal range of 64-83 g/L.) Most of the protein in the suspending media of the fresh RBC sample (0.92±0.08 g/L) and of the sample of stored RBCs washed in saline (2.52±0.14 g/L) is Hb. The concentration of Hb in the sample of unwashed stored RBCs (1.22±0.15 g/L) represented only a small fraction of the total protein. For reference, fresh blood plasma has an Hb concentration of 0.45±0.01 g/L measured using the same cyanohemoglobin assay.

The measured viscosity of the suspending medium among the samples of fresh RBCs (1.15±0.02 cP), washed stored RBCs (1.13±0.03 cP), and unwashed stored RBCs (1.06±0.06 cP) is not significantly different. For reference, fresh blood plasma has a viscosity of 1.70±0.05 cP, saline has a viscosity of 0.91±0.03 cP, and deionized water has a viscosity of 0.89±0.02 cP. The critical shear-stress values—a metric of RBC aggregation—are also not significantly different between the three samples: 139±3 mPa for fresh RBCs, 141±6 mPa for washed stored RBCs, and 131±4 mPa for unwashed stored RBCs (the critical shear-stress value for fresh whole blood sample is 291±8 mPa).

Example 12: Storage Induced Changes in Capillary Flow Rate

Figure 7A:
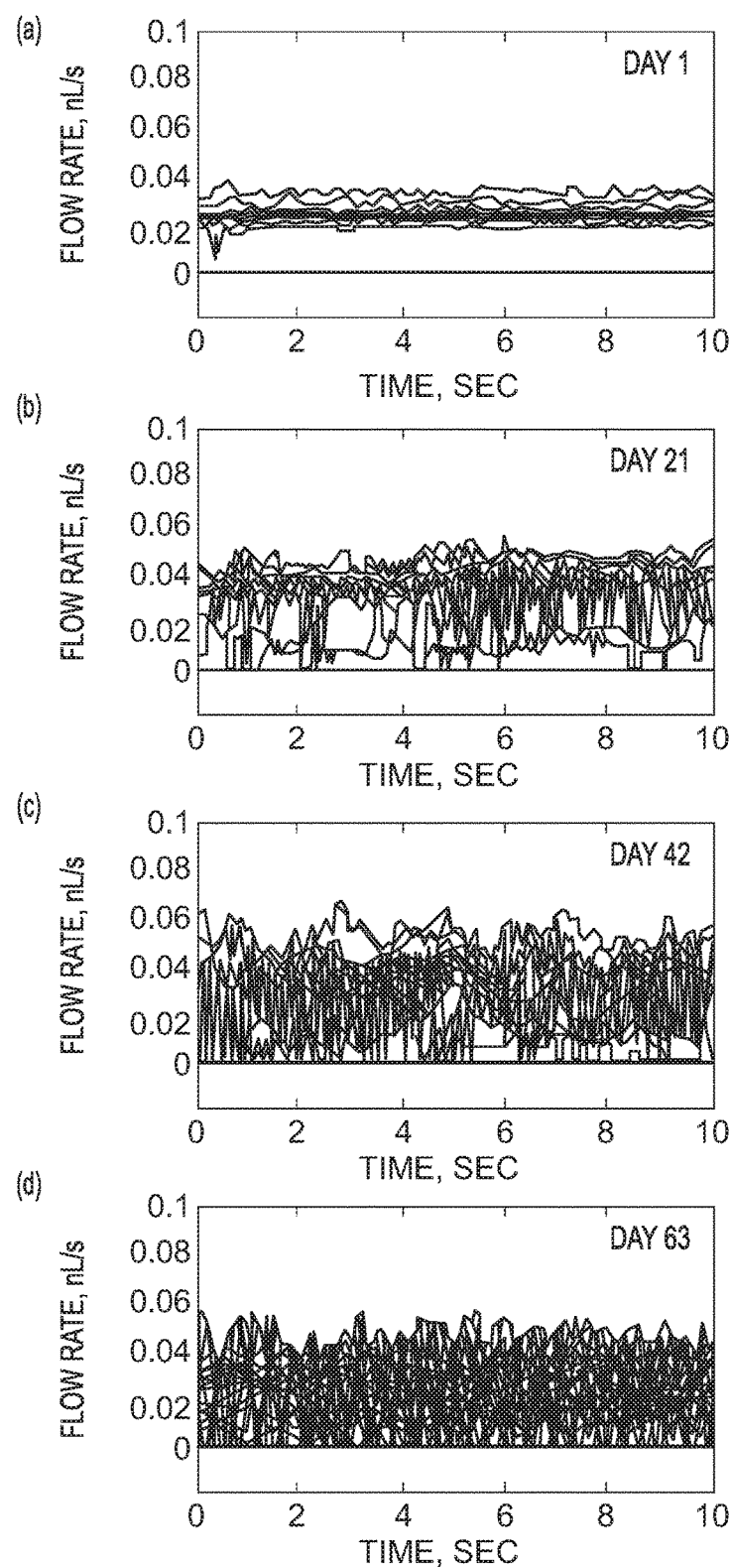
FIGS. 7A-7C illustrate network capillary flow traces of RBC in exemplary CNDs of blood stored up to 63 days in accordance with exemplary aspects.
Figure 7B:
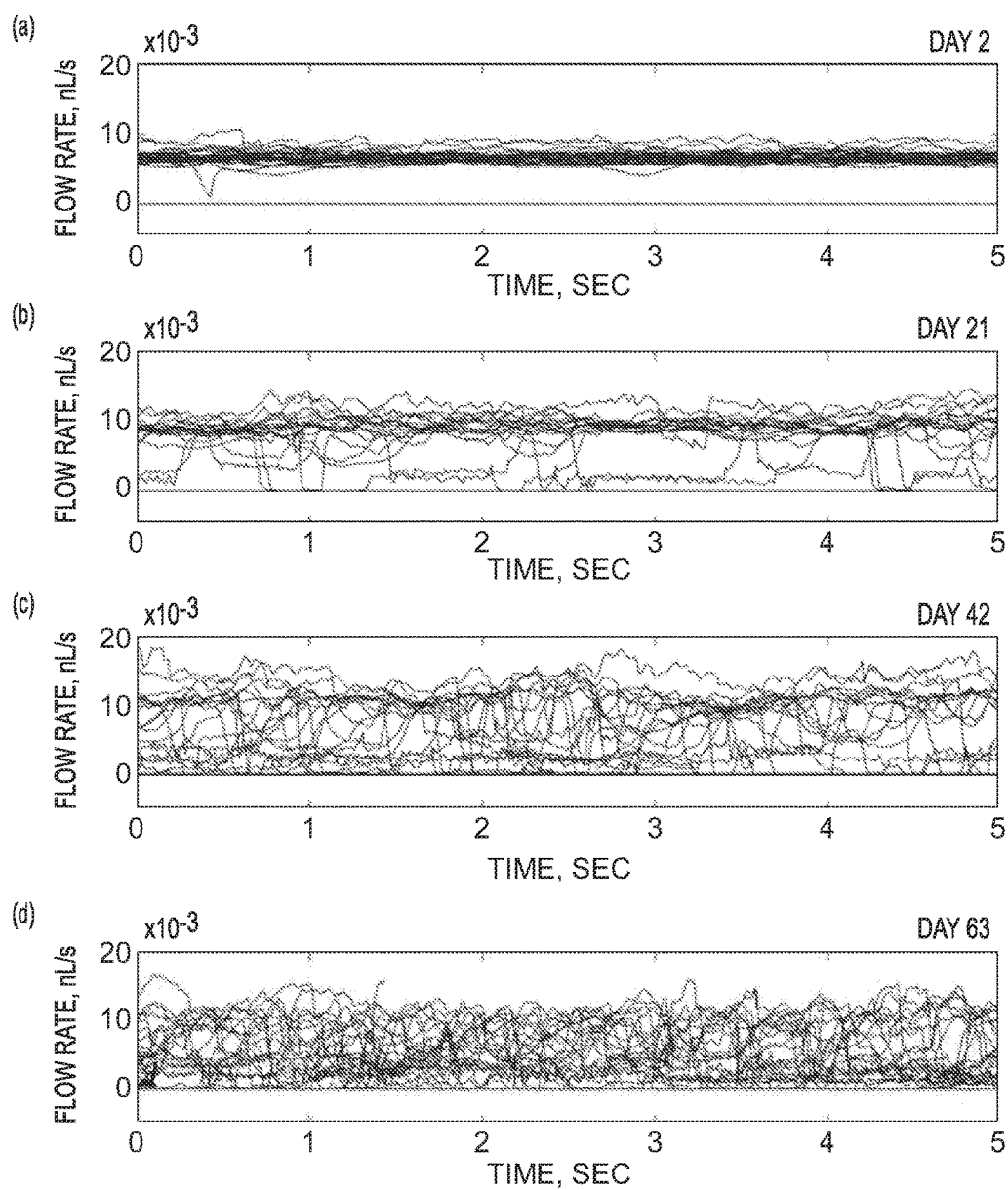
Figure 7C:
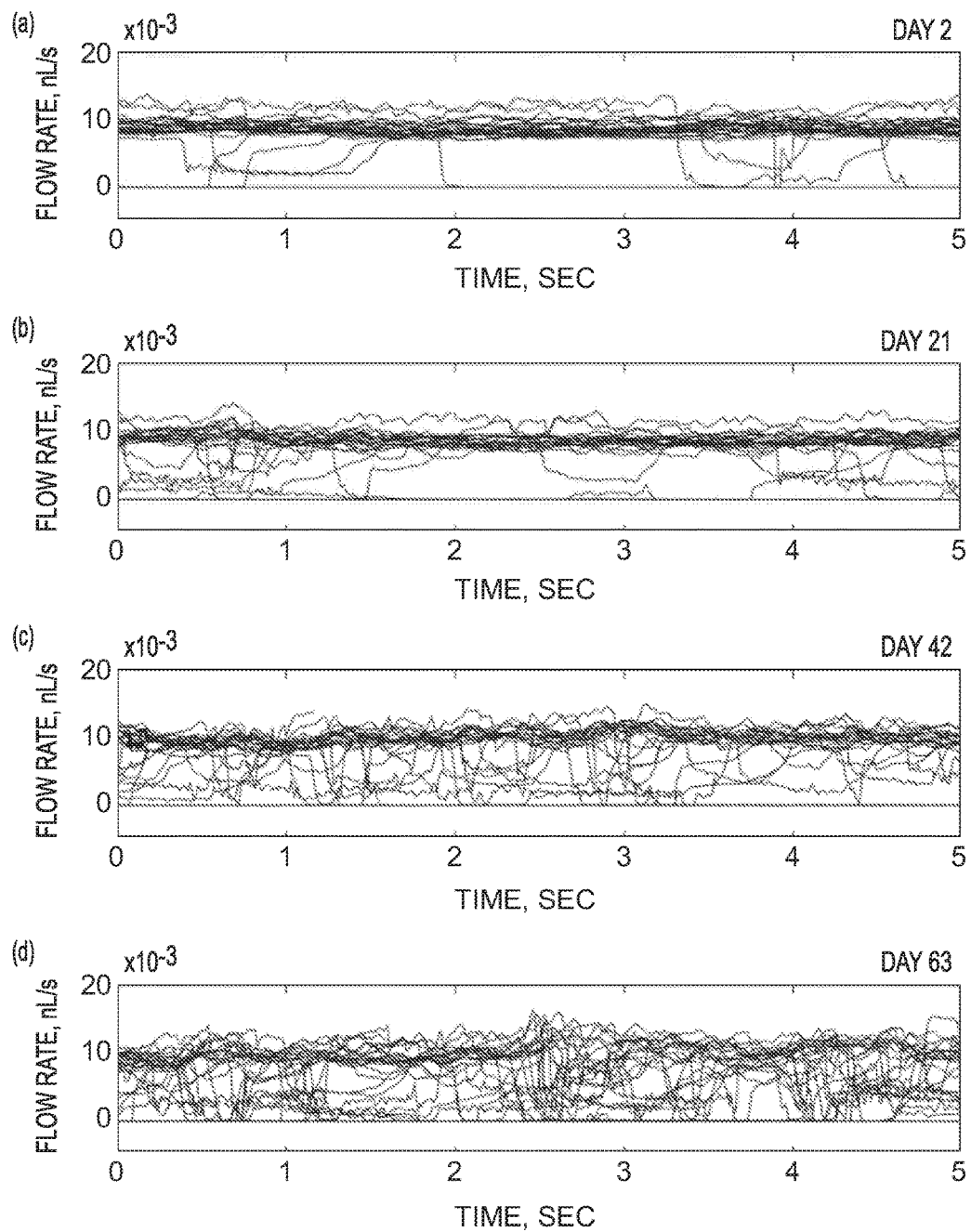

For each CND, a trace of the flow rates of the RBCs in each of the microchannels comprising the capillary network is determined. Network capillary flow traces of RBC samples followed a characteristic change in flow traces over the course of cold storage, as shown in FIGS. 7A-7C showing (a) 1 or 2 day(s), (b) 21 days, (c) 42 days, and (d) 63 days for each. Noticeably random "oscillation" of the flow rates in the microchannels is due to rigid cells slowing and/or plugging of some of the microchannels, and the "oscillations" in flow rates and plugging events increase with the duration of storage. During week 1 (FIGS. 7A(a), 7B(a), and 7C(a)), the flow traces of all microchannels are grouped tightly around a baseline flow rate displaying characteristics of a parametric distribution, but as the weeks progressed the flow traces of all the CND microchannels begin to become increasingly "oscillatory" (FIGS. 7A(b) to (d), 7B(b) to (d), and 7C(b) to (d)) with the baseline flow rate

TABLE 1

Characteristics of RBC samples that may affect CND perfusion measurements*
TABLE 1. Characteristics of RBC samples that may affect AMVN perfusion measurements*

| Characteristic | Fresh whole blood | RBC Samples | | | Saline | Water |
| --- | --- | --- | --- | --- | --- | --- |
| | | Fresh | Stored | Stored washed | | |
| Total protein concentration (g/L) | 68.21 (3.31) | 1.04 (0.06) | 9.95 (0.10)† | 2.85 (0.53)†‡ | 0.01 (0.00) | |
| Hb concentration (g/L) | 0.45 (0.01) | 0.92 (0.08) | 1.22 (0.15)† | 2.52 (0.14)†‡ | 0.02 (0.01) | |
| Viscosity (cP) | 1.70 (0.05) | 1.15 (0.02) | 1.06 (0.06) | 1.13 (0.03) | 0.91 (0.03) | 0.89 (0.02) |
| Aggregation (as critical shear stress, mPa) | 291 (8) | 139 (3) | 131 (4) | 141 (6) | | |

*Data are reported as mean (SD).
†$p < 0.01$ vs. fresh.
‡$p < 0.01$ vs. stored.

gradually disappearing as the data becomes skewed and non-parametric by week 9 (FIGS. 7A(d), 7B(d), 7C(d)).

Flow-rate traces in FIGS. 7A and 7B show the effect of the dynamic plugging as the flow rates in all the 32 microchannels progressively deviate from a baseline value (Day 2) with increasing storage times. For both samples on Day 2 (FIGS. 7B(a), 7C(a)), the flow traces of all the microchannels display a bimodal distribution (where a large population is tightly grouped around a baseline flow rate, while a small population of the RBCs plug—transiently or completely—the individual microchannels of the network). However, as the weeks progress, the flow traces of all the microchannels begin to increasingly fluctuate, and by Day 63 the normal distribution around the baseline flow rate gradually became less defined for the anaerobic sample (FIG. 7C(d)) and nearly disappeared for the conventional sample (FIG. 7B(d)). The increase in the random fluctuations of the flow rates are due to an increase in the number of poorly deformable RBCs slowing and/or plugging the flow through the microchannels. The data from FIG. 7 are used to construct the histograms in FIG. 8A, which depict in more detail the sample population densities of the RBC flow rates in the microchannels of Device A.

Figure 8A:
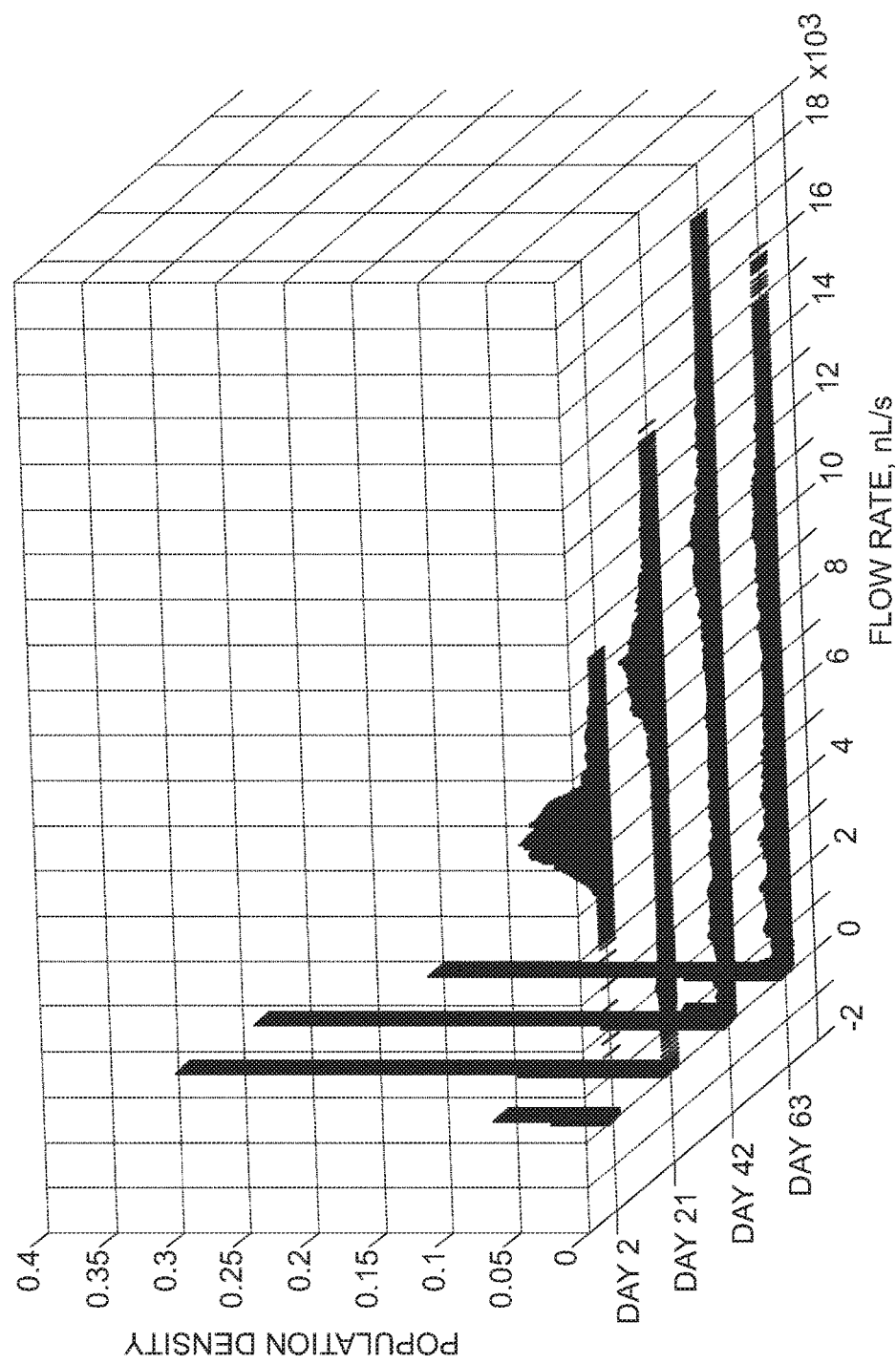
FIGS. 8A-8B illustrate population densities of the RBC flow rates in an exemplary CND according to the present disclosure for RBCs stored aerobically (A) and anaerobically (B).
Figure 8B:
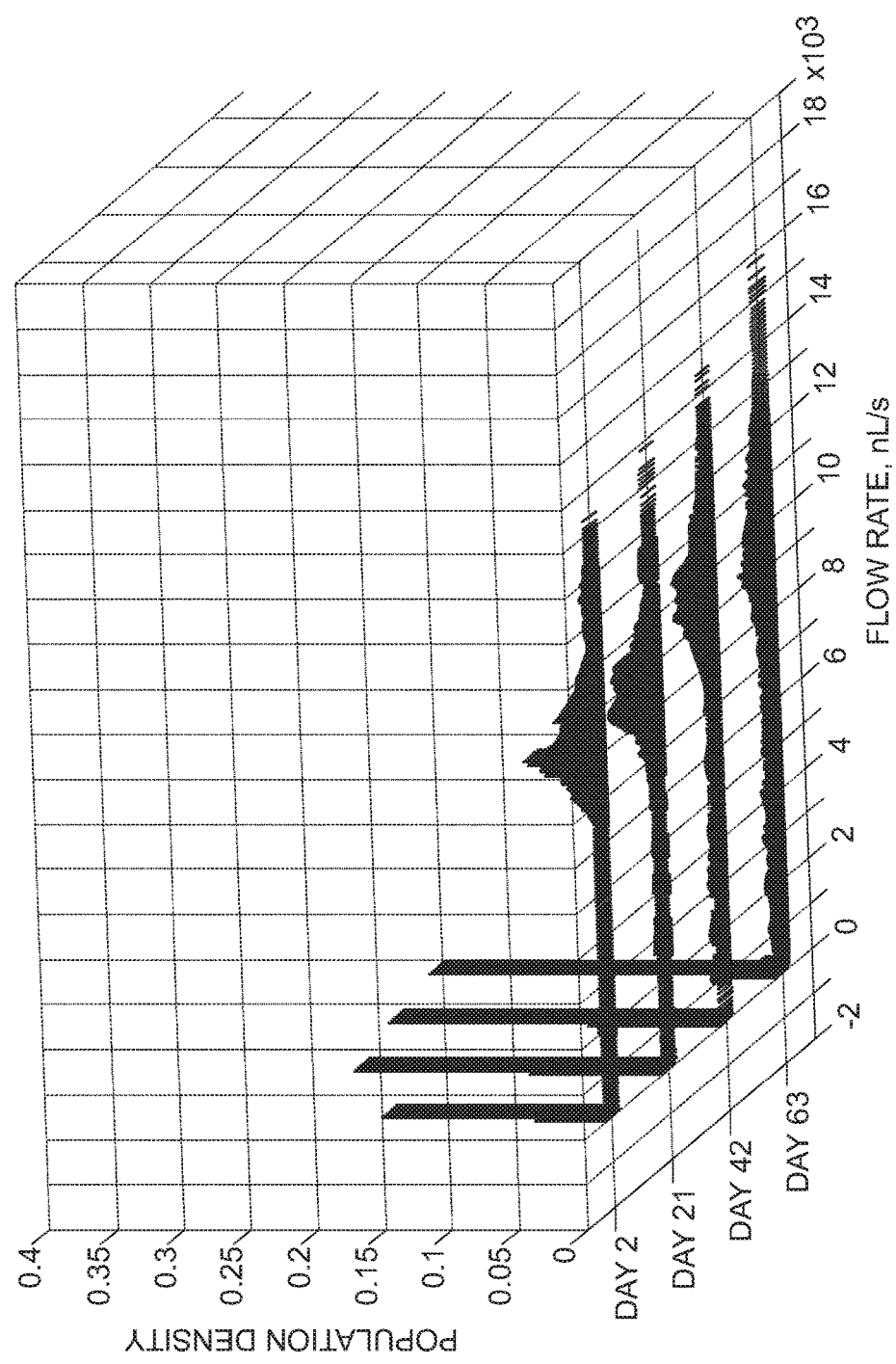

FIG. 8A and FIG. 8B show the bimodal distribution of the flow rates for conventionally and anaerobically stored RBCs as they traverse through all the 32 microchannels within a single network in CND-A. In FIG. 8A, it can be observed that, at Day 2, the majority of the flow rates for conventionally stored RBCs are normally distributed around a mean of 6.4 pL/s. However, by Day 63 the normal distribution disappears and the number of lower flow and no flow RBCs dramatically increase. FIG. 8B shows the normal distribution of flow rates for the anaerobically stored RBCs at Day 2 centered around a mean of 8.3 pL/s. However, in contrast to conventionally stored RBCs, a good fraction of anaerobically stored RBCs maintain their normal distribution at a high flow state on Day 63 of storage (55% for anaerobic vs. 37% for conventional RBCs).

In FIG. 8, a bimodal distribution of the flow rates of the RBCs passing through all 32 microchannels within a single network in CND-A for RBCs stored conventionally (FIG. 8A) and anaerobically (FIG. 8B) is observed. Not to be limited by theory, this bimodal distribution is due to the transient plugging of the microchannels which correlates to the inability of a small subpopulation of the RBCs to readily deform. The dynamics of blood flow in these networks at this pressure difference (20 cmH$_2$O) are interesting; the networks do not become completely plugged by the stored RBCs (although they could be) nor are the shear stresses high enough to rupture the cells—the cells either pass through (with fluctuations in velocity as the resistance changes) or simply become lodged in the capillary. Because the microchannels are in parallel and hydrodynamically connected to each other, the flow rates in the individual microchannels are constantly changing in reaction to the changing resistances due to deformability of the RBCs "locally" (in the capillary) and "from a distance" (in adjacent microchannels). The total increase in resistance reduces the overall bulk flow rates, but does not completely diminish the bulk flow rate like in a typical micropore filter. Filtration commonly involves the use of a 3 µm or 5 µm nucleopore filter ($\approx 4 \times 10^5$ pores/cm$^2$) through which a 0.5 mL suspension of 1 to 20% hematocrit is passed through (usually $\Delta P$ is not constant); the bulk flow rate of the RBCs through the filter are measured. The bulk flow rate goes to zero over time and is limited by the number of pores, pore size, the number of cells and the sphericity of the cells (cell size). The filtration technique for measuring the deformability of RBCs is not physiologically relevant. In comparison, the RBCs in our network device are at a physiologically relevant hematocrit, pressure difference, and the flow rates are comparable to those seen in vivo under the same conditions (Q$\approx$0.01 pL/s); in addition, the networks are structured in an architecture that more closely mimics microvasculature in vivo than the micropore filters. The microchannels in the network usually remain in an "open" state due to the geometry and gentle narrowing of the microchannels, and the fluctuating flow rates in adjacent channels. Because these networks do not plug as easily as the micropore filters and flow in near-physiological conditions, the network devices measure a larger dynamic range of flow rates (RBC deformability).

FIG. 8 shows that a larger number of RBCs can maintain their high flow state by Day 63 (with flow rates>mean minus 2SD of the Day 2 sample) in the anaerobically stored RBC unit than in the conventionally stored RBC unit, which is universally true for all the RBC units tested. A small, distinct subpopulation of RBCs (with flow rates<mean minus 2SD of the Day 2 sample) is much less deformable than the rest of the RBCs environments of storage. Not to be limited by theory, this subpopulation may be the 'older' RBCs of the donated unit (i.e., RBCs nearing the end of their lifecycle of ~120 days when first collected).

Example 13: Comparison of AMVN Device with Conventional Techniques

An AMVN device is compared with micro-pore filtration and ektacytometry, two conventional techniques frequently used for assessing RBC deformability.

(1) Micro-pore filtration assay: RBC filterability is evaluated by measuring the time it takes a known volume of a dilute RBC suspension to pass through a thin polycarbonate membrane containing about 10$^6$ of 5 µm pores. This measurement is known to be sensitive primarily to the size and sphericity (surface area to volume ratio) of individual RBCs, but has been shown to not reflect the internal cell viscosity. The micro-pore filtration assay may be confounded by its extreme sensitivity to pore plugging by residual leukocytes and cellular clumps contaminating the tested sample and/or by a small fraction of non-deformable RBCs.

(2) Ektacytometry: In this technique, the deformability of RBCs is evaluated by measuring elongation of RBCs suspended at <0.5% hematocrit in a highly-viscous solution of polyvinylpyrrolidone (PVP) and subjected to a well-defined shear stress field. Ektacytometry at low shear stress (3 Pa) is known to be sensitive to RBC membrane properties, and at high shear stress (17 Pa)—to so-called "maximal deformability," which is defined by the RBC surface area to volume ratio. The measurement of RBC deformability using ektacytometry may be confounded by several important factors, including: (a) the viscosity of the PVP solution is about 30-times larger than that of plasma, which is not physiological and thus completely changes the mechanical response of RBCs to shear (RBCs subjected to shear in plasma flip, not elongate), and (b) the hematocrit of RBC suspension is extremely low and thus ektacytometry does not account for RBC deformations due to cellular collisions (which are abundant in real blood).

(3) An AMVN device of the disclosure is used to enable a direct assessment of the ability of stored RBCs (suspended in a normal viscosity medium at 40% hematocrit) to perfuse a microvascular network, which is an integrative metric of RBC capacity to undergo deformations in microchannels of different sizes and due to cellular collusions, and RBC aggregability.

RBC units (CPD/AS-1, leukoreduced) are acquired on Day 3 after donation, each RBC unit is split into two half-volume units, and one of the split units is passed through the Hemanext® de-oxygenation device into the oxygen-impermeable bag for anaerobic storage (both to be provided by New Health Sciences, Inc). The other (unprocessed) split unit serves as conventional (aerobic) control.

Both units are stored at 1-6° C. in a blood bank refrigerator (Jewett BBR6-1B18) for 6 weeks, and a comprehensive assessment of RBC deformability is performed for samples drawn upon receipt of each original RBC unit from the Blood Center (Day 3), and after 1, 2, 4, and 6 weeks of storage. Deformability of RBCs stored anaerobically (Hemanext®) and aerobically (conventional storage) is measured with three complementary methodologies:

(1) AMVN, to measure network perfusion rate (as described above).

(2) Ektacytometry, to measure the elongation index at 3 Pa and 17 Pa shear stress (RheoScan-D300, Korea).

(3) Micro-pore filtration assay, to measure the filtration time for a 5 µm polycarbonate filter.

Figure 9:
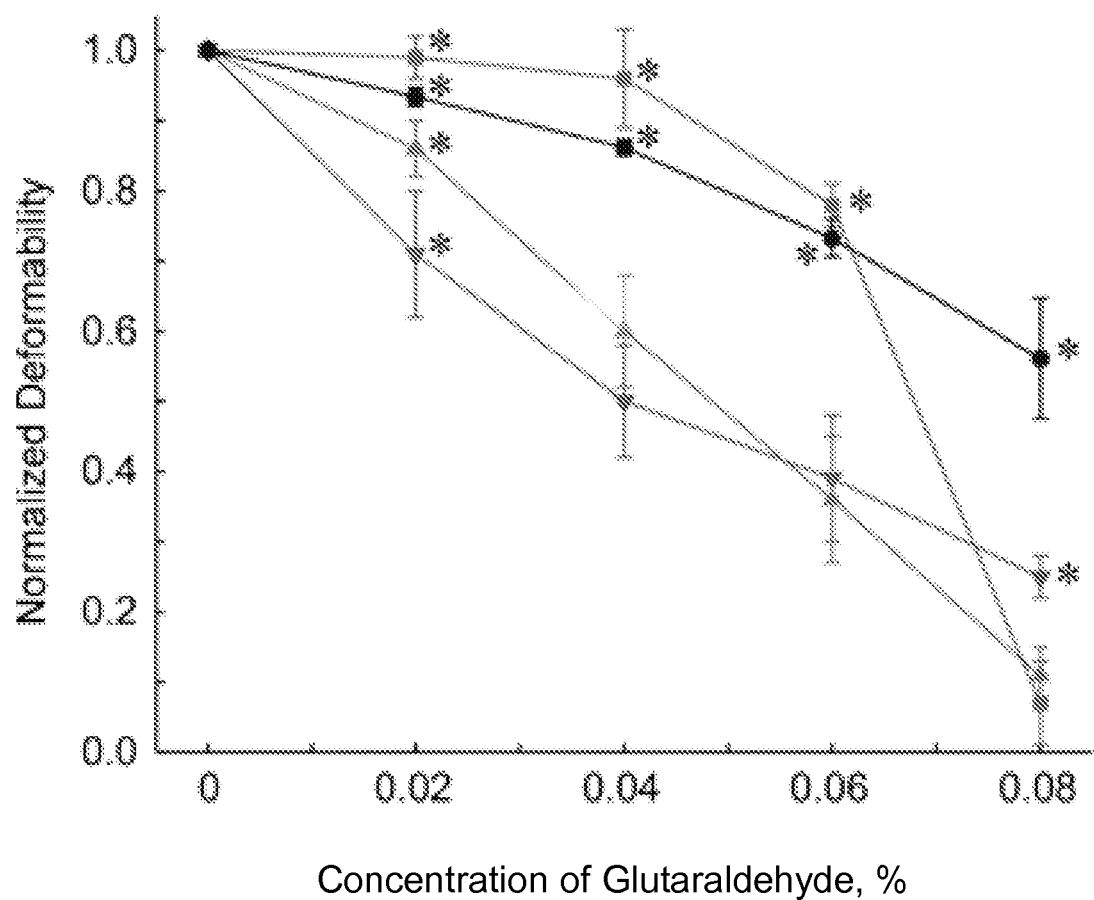
FIG. 9 illustrates a comparison of RBC deformability measurements in vitro using a CND, a 5 µm filter, and a Rheoscan under low shear (3 Pa) and high shear (17 Pa) conditions.
Figure 10A:
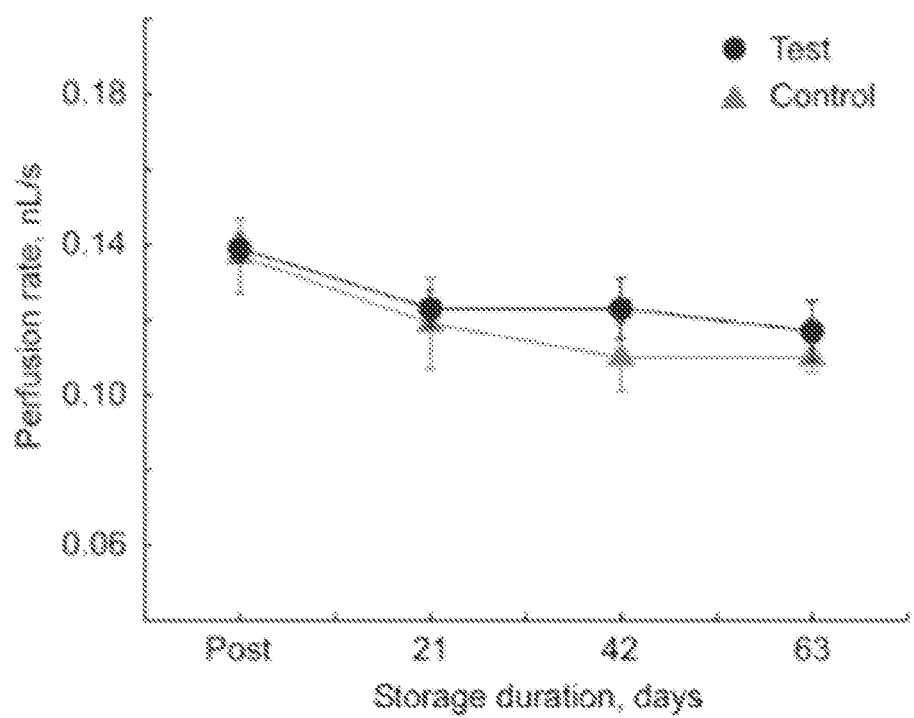
FIGS. 10A-10C illustrate perfusion rates for anaerobically and aerobically stored blood obtained from CNDs according to exemplary aspects.
Figure 10B:
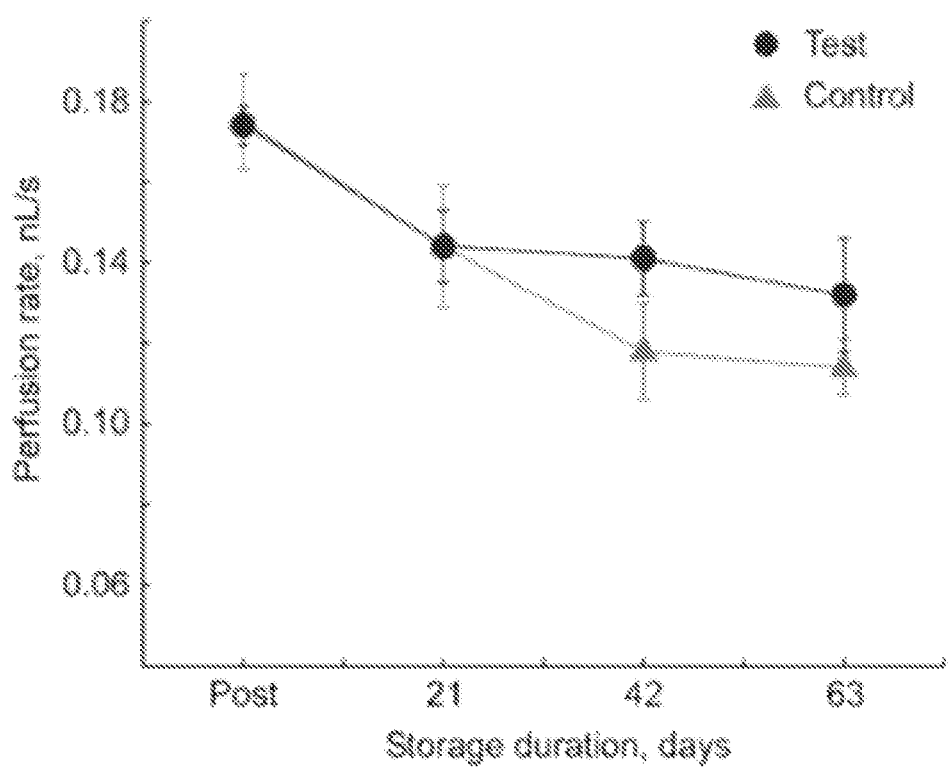
Figure 10C:
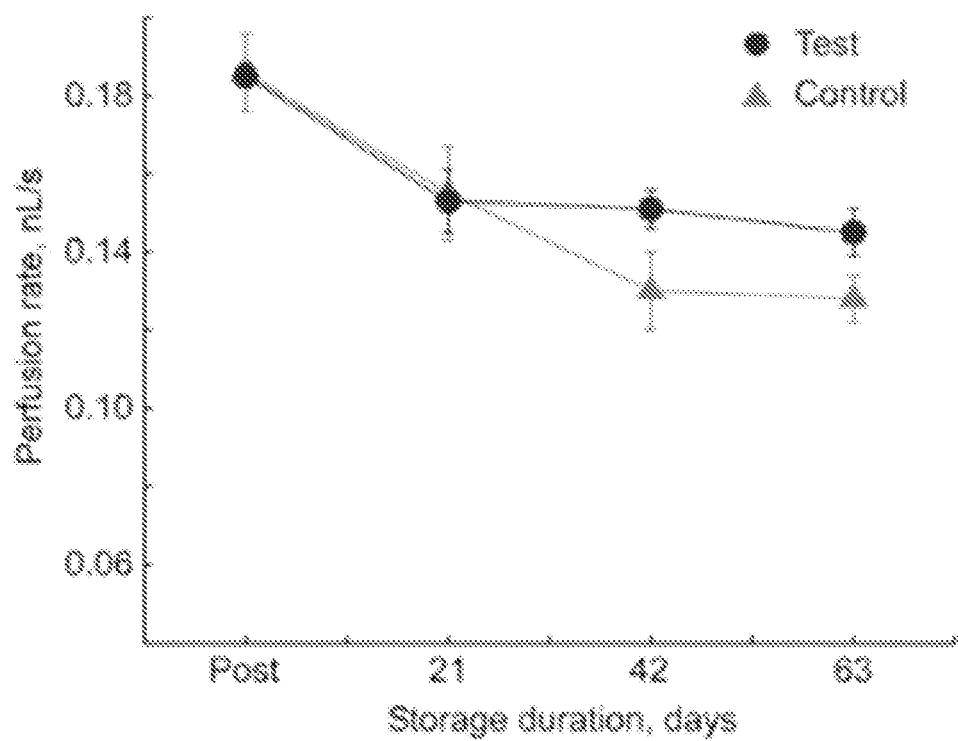

The results of the assays are presented in FIG. 9.

Example 14: RBC Storage-Induced Changes in Bulk Network Flow Rate

Figure 11A:
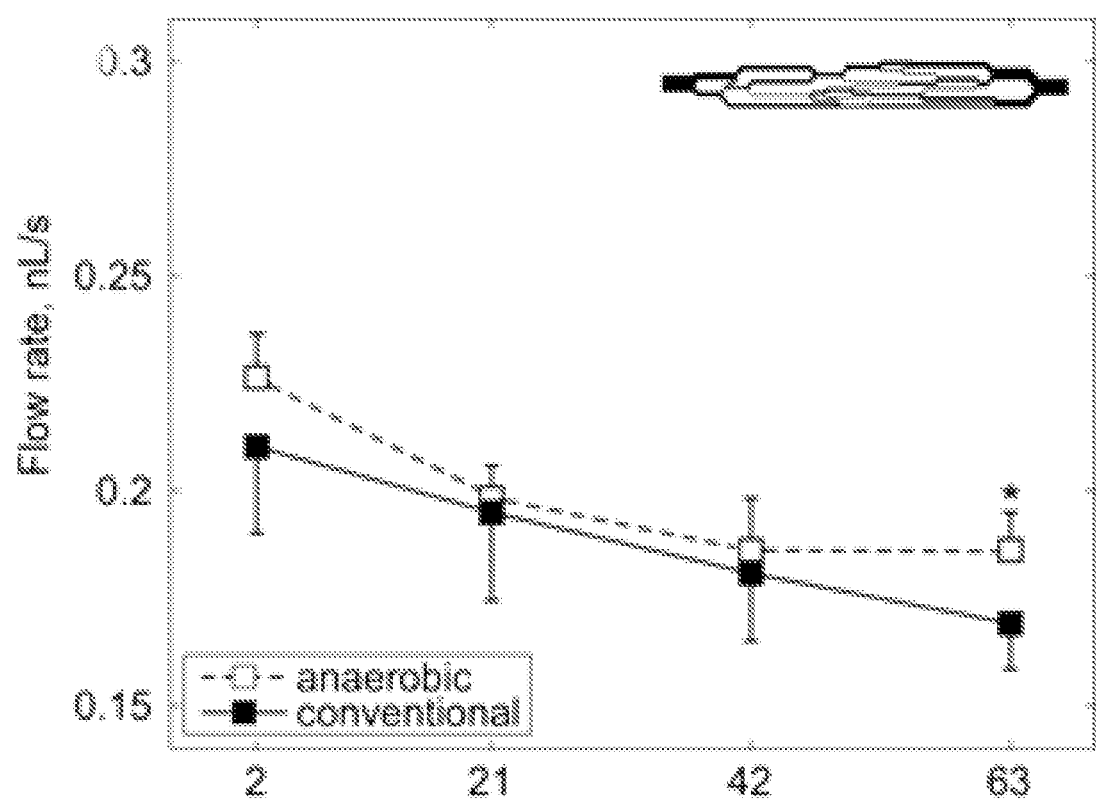
Figure 11B:
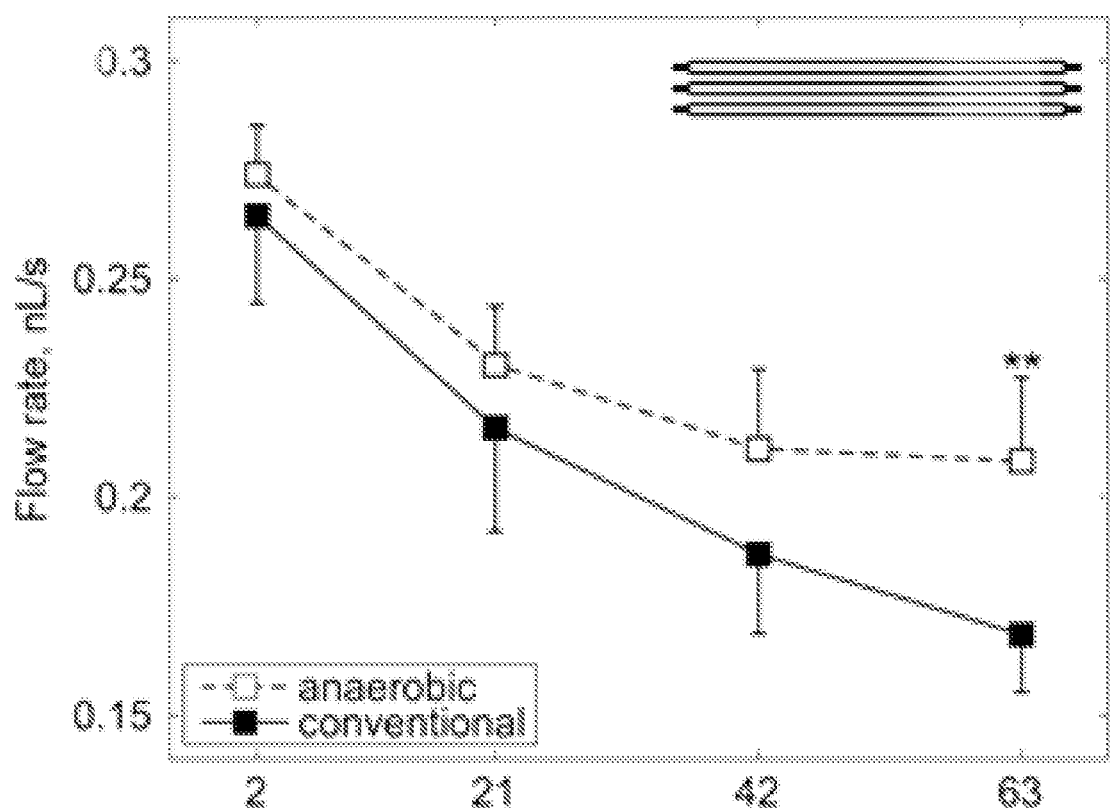

The effect of anaerobic storage conditions on mechanical properties of stored RBC, as reflected in their ability to perfuse the microfluidic devices is investigated. Device perfusion for matched pairs of blood units (n=4-8) is measured by quantifying the rate of blood flow in venules of (a) the AMVN device of FIG. 1A (b) the CND-A device of FIG. 1B and (c) the CND-A device of FIG. 1C, at a pressure difference of −20 cmH$_2$O. With reference to FIGS. 11A-11B, a significant decline in the bulk flow rate for both RBC units in both devices at a pressure difference of −20cmH$_2$O is observed, as well as a significant difference in the storage-induced decline in the bulk network flow rate between the aerobic and anaerobic RBC units at a pressure difference of −20cmH$_2$O. —asterisk (*) represents a statistically significant (p<0.01) difference between anaerobic and conventional (aerobic) storage of the same duration. Values are means±SD.

Figure 12A:
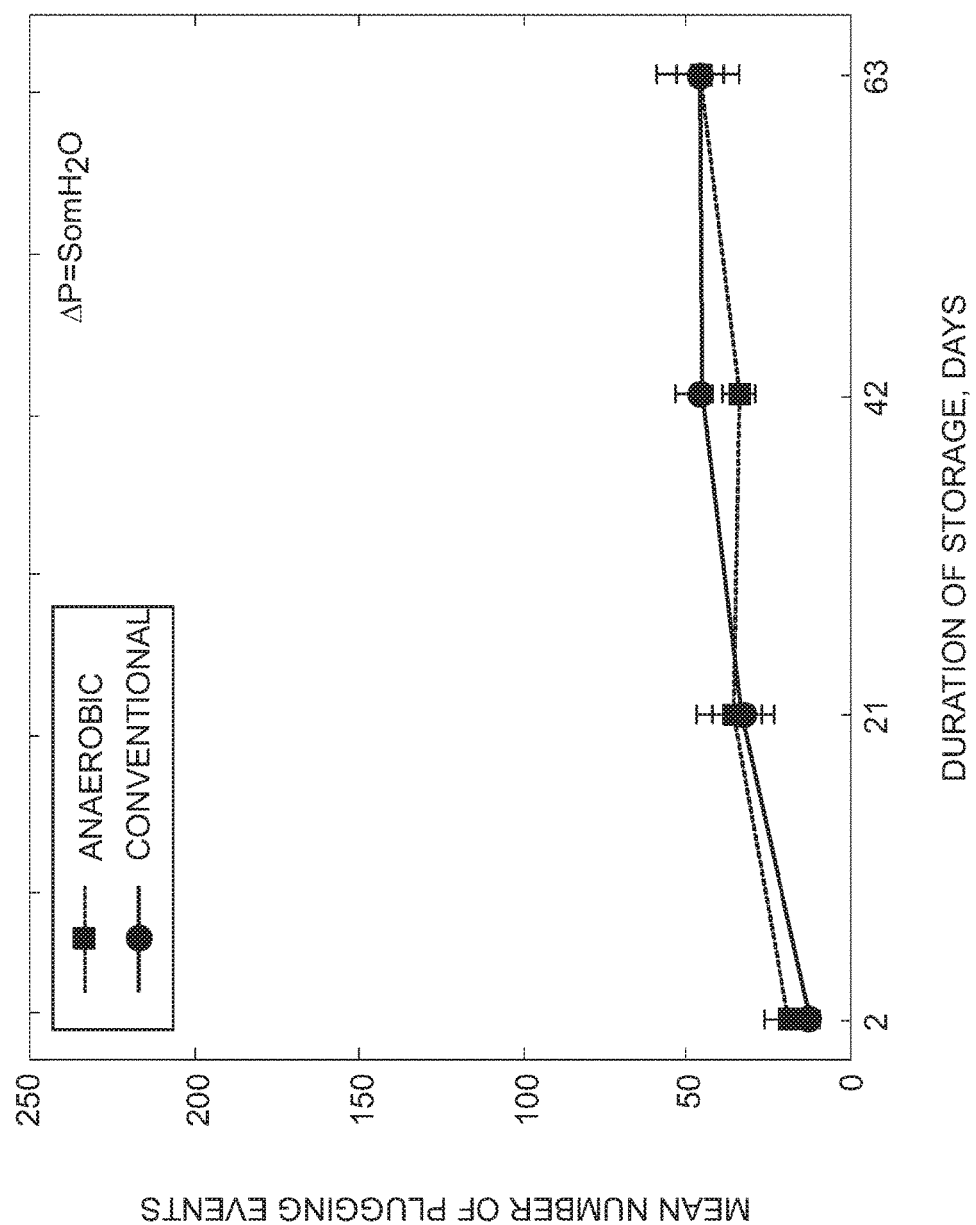
FIGS. 12A-12C illustrate plugging rates for anaerobically and aerobically stored blood obtained from CNDs according to exemplary aspects.
Figure 12B:
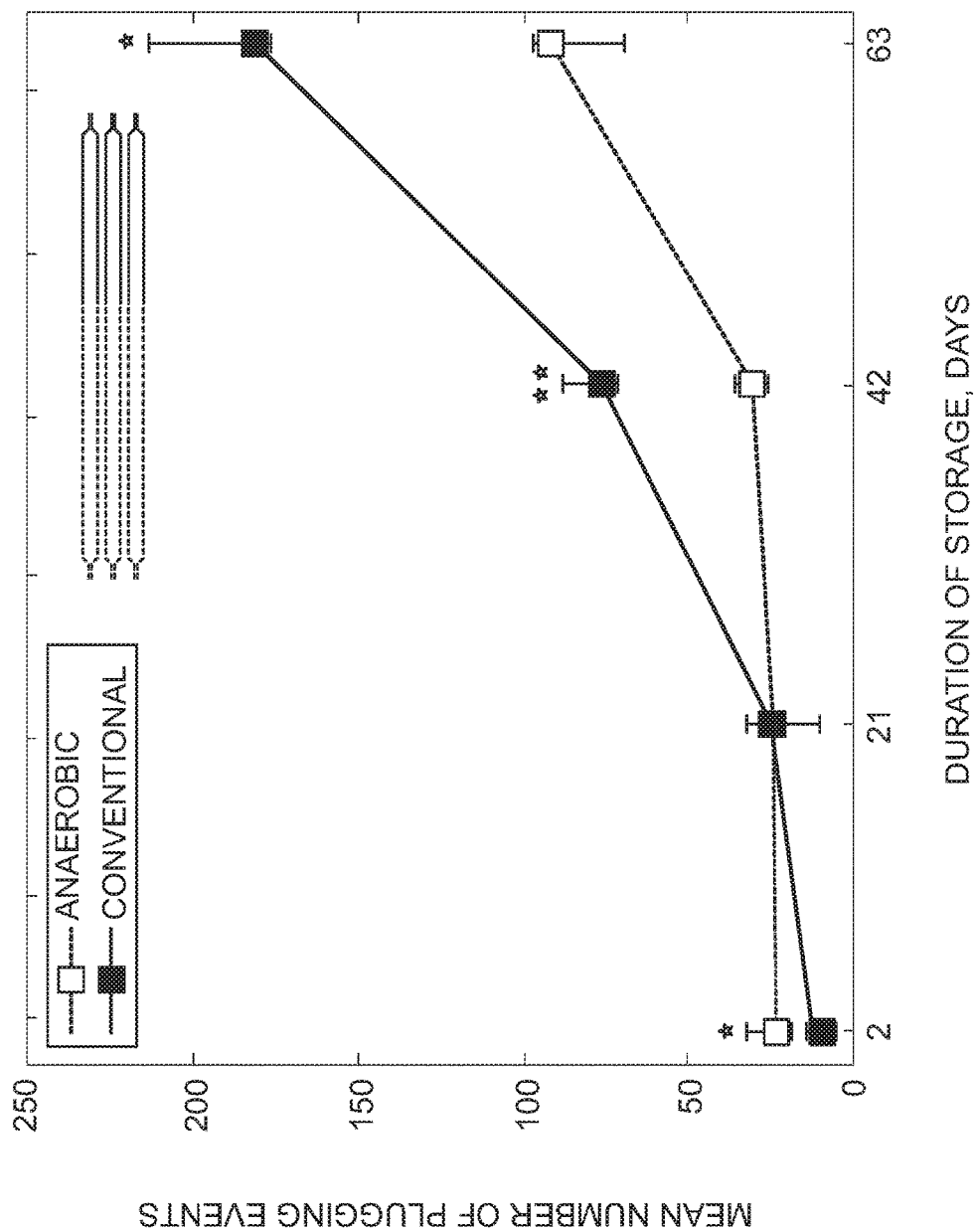
Figure 12C:
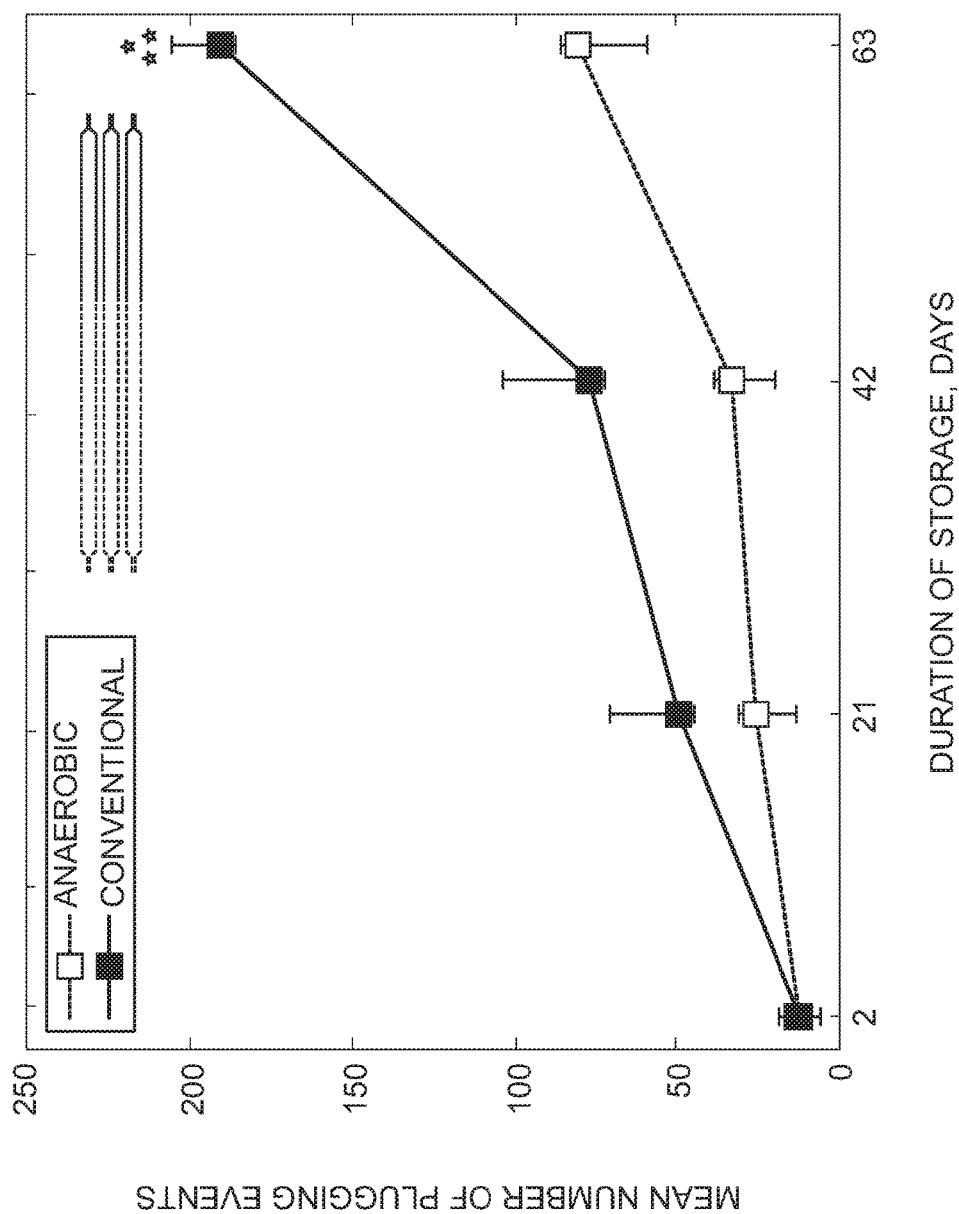

From the traces of capillary flow rates in the time-dependent domain, the mean number of plugging events in the whole capillary network for each RBC sample is determined (FIGS. 12A-12C). RBCs from the same donor (matched pair) stored conventionally and anaerobically are passed through the networks of an AMVN device of FIG. 1B. Total number of plugging events that occurred in the microchannels of a single network during a 10 second interval are counted at pressure differences of (a) −20 cmH$_2$O, (b) −10 cmH$_2$O, and (c) −5 cmH$_2$O. Plugging events refers to the number of times the velocity of the RBCs (conventional and anaerobic) in the capillary becomes below the Ave.±3 S.D. of the Day 1 sample, respectively. Notice the increase in the number of plugging events as the duration of storage increases for both samples, however, RBCs stored conventional display more plugging events on average.

A significant increase in the mean number of plugging events from Week 1 to Week 9 is found for both RBC units for CND-A and CND-B devices at all three pressure differences of (a) −20 cmH$_2$O, (b) −10 cmH$_2$O, and (c) −5 cmH$_2$O; however, the mean number of plugging events (NPE) for RBCs stored conventionally (aerobically) was significantly higher than RBCs stored anaerobically on Day 43 and Day 64 at a pressure difference of −20cmH$_2$O and −10 cmH$_2$O.

Figure 11C:
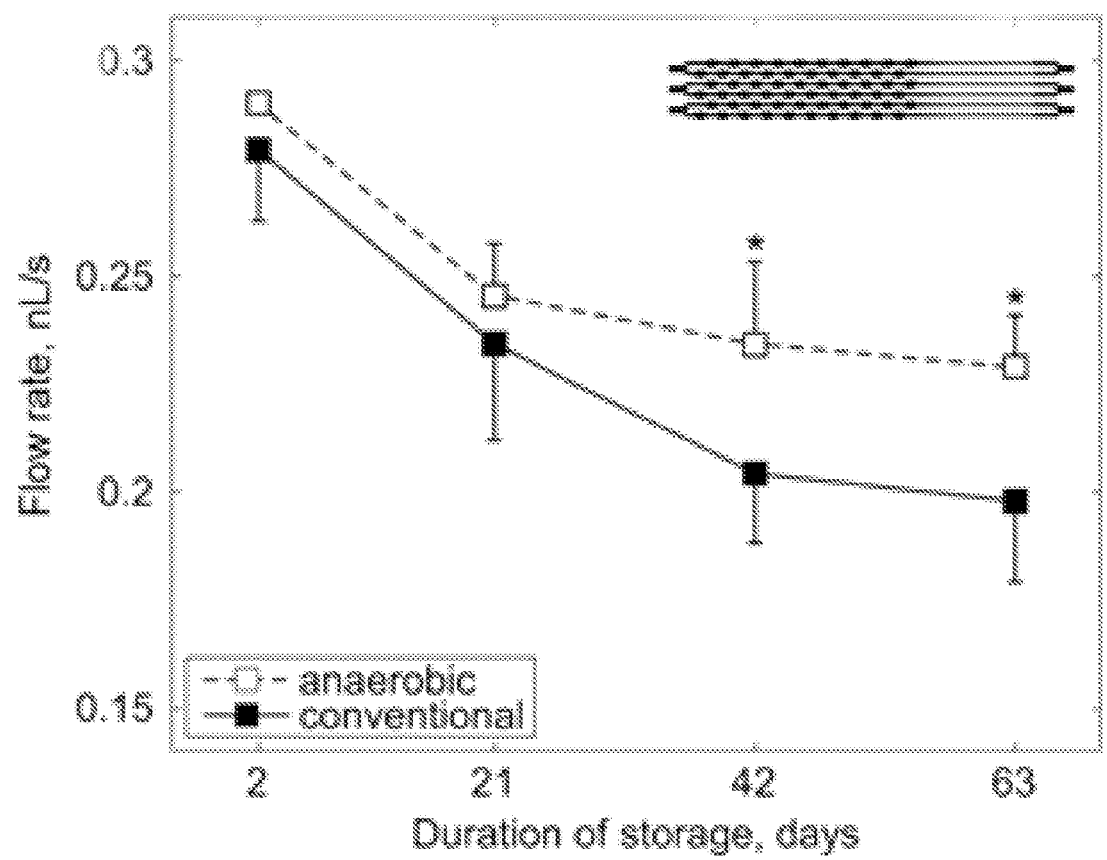

A significant reduction is observed in the bulk flow rates over the duration of storage for both conventionally stored RBC units and anaerobically stored RBC units in all three networks devices (FIGS. 11A-11C). The reduction in the perfusion rates with storage was expected, however, the anaerobically stored RBCs exhibit lesser reduction over storage times and in fact seem to perform better than their younger conventional counterparts.

FIG. 11A shows the changes in the bulk flow rate of both the control and test RBC samples with storage times, measured using the AMVN network device. There is a significant decline of 10% by Day 42 (p<0.01), and 14% by Day 63 (p<0.001) in the mean bulk network flow rate of conventionally stored RBCs compared to the Day 2 sample. For the anaerobically stored RBCs, there is a significant decline of 10% by Day 21 (p<0.001), 14% by Day 42 (p<0.001), and 14% by Day 63 (p<0.001). However, anaerobically stored RBCs, in comparison to the conventionally stored RBCs of same nominal age, have a significantly higher mean bulk flow rate by 6% on Day 63 (p<0.01).

FIG. 11B shows the changes in flow rates of control and test RBC samples measured by CND-A. There is a significant decline of 17% by Day 21 (p<0.01), 27% by Day 42 (p<0.001), and 33% by Day 63 (p<0.001) in the mean bulk network flow rate of conventionally stored RBCs compared to the Day 2 sample. For the anaerobically stored RBCs, there is a significant decline of 15% by Day 21 (p<0.001), 22% by Day 42 (p<0.01), and 23% by Day 63 (p<0.001). Again, anaerobically stored RBCs, in comparison to conventionally stored RBCs of the same nominal age, have a significantly higher mean bulk flow rate by 14% on Day 63 (p<0.01). Additionally, anaerobically stored RBCs have a significantly higher mean bulk flow rate by 7% (p<0.05) on Day 63 vs. the Day 42 (i.e. 3 week younger) conventionally stored RBCs.

FIG. 11C shows the changes in the flow rate of control and test RBC samples as measured by CND-B. There is a significant decline of 15% by Day 21 (p<0.01), 26% by Day 42 (p<0.001), and 28% by Day 63 (p<0.001) in the mean bulk network flow of conventionally stored RBCs, rate compared to the Day 2 sample. For the anaerobically stored RBCs, there is a significant decline of 15% by Day 21 (p<0.001), 19% by Day 42 (p<0.05), and 21% by Day 63 (p<0.001). Again, anaerobically stored RBCs, in comparison to conventionally stored RBCs of the same nominal age, have a significantly higher mean bulk flow rate by 10% on Day 42 (p<0.05) and 11% on Day 63 (p<0.05). In addition, anaerobically stored RBCs have a significantly higher mean bulk flow rate by 8% (p<0.05) on Day 63 vs. the Day 42 conventionally stored RBCs.

The mean "number of plugging events" (NPE) in the whole network of CND-A and CND-B for each RBC sample is determined and shown in FIGS. 12B and 12C, respectively. The 5 second traces of capillary flow rates are used to count the total number of "plugging events" for each sample and the number is averaged across units for their respective length of storage. "Plugging events" are counted by first determining a baseline 'cut off' value for each unit—the baseline "cut-off" value (mean flow rate minus 2SD) is the mean flow rate of the RBCs in all the microchannels that are unplugged (flow rates>0) in a single network unit for the Day 2 sample. The number of times the flow rate in each channel dipped below the baseline "cut-off" value is counted to determine the mean NPE for the Day 2, 21, 42, and 63 samples of the sample unit. The mean NPE from Day 2 to Day 63 for both RBC units in both devices is observed; however, the mean NPE for RBCs stored conventionally is significantly greater than the RBCs stored anaerobically on Day 42 and Day 63.

FIGS. 12A to 12C show the increase in the mean number of plugging events with storage time for both AMNV, CND-A and CND-B, respectively. For the conventionally stored RBCs, there is a significant increase of 3× by Day 21 ($p<0.05$), 9× by Day 42 ($p<0.001$), and 21× by Day 63 ($p<0.05$) in the mean NPE compared to the Day 2 sample (FIG. 12B); for the anaerobically stored RBCs, there is a significant increase of 3× by Day 63 only ($p<0.01$). Conventionally stored RBCs, in comparison to anaerobically stored RBCs of the same nominal age, have a significantly higher mean NPE of 2× by Day 42 ($p<0.01$) and of 2× by Day 63 ($p<0.05$); however, anaerobically stored RBCs have a significantly higher mean NPE of 3× by Day 2 ($p<0.05$).

For the conventionally stored RBCs, there is a significant increase of 6× by Day 42 ($p<0.05$) and 16× by Day 63 ($p<0.01$) in the mean NPE compared to the Day 2 sample; for the anaerobically stored RBCs, there is a significant increase of 2× by Day 42 ($p<0.05$) and 2× by Day 63 ($p<0.01$) (FIG. 12C). Conventionally stored RBCs, in comparison to anaerobically stored RBCs of the same nominal age, had a significantly higher mean NPE by 2× on Day 63 ($p<0.001$).

The differences observed in the bulk perfusion rates between the AMVN device and, collectively, CND-A and CND-B (since they are not significantly different from each other) are due to the design of their artificial microvascular networks. In the AMVN, the majority of the RBCs, both highly- and poorly-deformable, tend to flow along the streamlines of the high flow, large diameter channels—in this case, the poorly-deformable (more rigid, spherical) RBCs reduce network perfusion only by increasing the relative viscosity of the blood due to their collective disturbance of the flow (these RBCs are less able to change their shape to minimize the driving pressure/maximize the flow). However, in the networks of CND-A and CND-B, in addition to the effect of rigid RBCs on relative viscosity, every individual RBC is forced to deform through a capillary in single file under high shear stress—in this case, the poorly-deformable RBCs reduce network perfusion by directly slowing, and in some cases stopping, flow in the microchannels. To reiterate, the bulk flow rates are only a collective measurement of the ability of the total RBC sample to deform and are not informative as to the presence of a subpopulation of RBCs that may lose their deformability more quickly, and affect the overall bulk flow rates more significantly, than other RBCs. The flow rates of the RBCs in the individual microchannels of CND-A and CND-B are measured to determine their effect on the overall flow of the RBCs through the network (bulk flow).

The bulk network flow rates in CND-A and CND-B are directly dependent on the flow rates in individual microchannels. Individual, non-deformable RBCs damaged in hypothermic storage transiently plugged a significant number of the microchannels where they narrowed to 3 μm in width, as depicted in FIGS. 1D and 1E. Not to be limited by theory, transient plugging of these microchannels and the associated increases in fluidic resistance (caused by cell-cell and cell-wall interactions) cause significant changes in the flow rates of the other parallel microchannels of the array—causing 'fluctuating' traces of the flow rates (FIG. 7)—and reduces the overall bulk flow of the RBCs through the network (FIGS. 11Bb, C).

In FIG. 12, the results of quantitatively counting the number of "plugging events" (NPE) that occurred across all RBC samples in the microchannels of CND-A (FIG. 12B) and CND-A (FIG. 12C). The increase in the mean NPE that occurs over the duration of storage is due to a dramatic increase in the initially very small population of poorly deformable RBCs, which has a large effect on the overall bulk flow rates for the entire network of microchannels in CND-A and CND-B.

Anaerobic storage better maintains the original level of deformability of a larger proportion of stored RBCs than conventional storage, and that CND-A and CND-B may be more useful in determining how individual cells may behave within the spleen and in the smallest of microchannels (and their dynamic effect on bulk network flow) in vivo than the AMVN.

Although the foregoing describes various aspects by way of illustration and example, the skilled artisan will appreciate that various changes and modifications may be practiced within the spirit and scope of the present application.

What is claimed is:

1. An artificial microvascular network device for a biological sample comprising:
a substrate having a capillary network formed thereon;
wherein said capillary network comprises at least one unbranched microchannel of a variable cross-sectional width along its length; at least one inlet port in communication with said capillary network microchannel for sample entry; and at least one outlet port in communication with said capillary network microchannel for sample exit; wherein the at least one unbranched microchannel ranges in a cross-sectional width from 3 μm to 70 μm; and
wherein said variable cross-sectional width is oriented along the longitudinal axis of said unbranched microchannel and comprises two or more expanded regions separated by a spacer, or two or more expanded regions separated by a spacer and a gradual taper having an initial width greater than a final width and a taper length ranging from 5 to 100 μm.

2. The device of claim 1, wherein said gradual taper comprises said initial width of about 30 μm and said final width of about 3 μm.

3. A capillary network device (CND) for a biological sample comprising:
a substrate;
one or more inlet ports for sample entry formed on said substrate;
one or more inlet microchannels formed on said substrate in communication with said one or more inlet ports for sample entry;
one or more outlet microchannels formed on said substrate in communication with said one or more inlet microchannels; and
one or more outlet ports formed on said substrate in communication with said one or more outlet microchannels;
wherein at least one of said one or more inlet microchannels or said one or more outlet microchannels is an unbranched microchannel having one or more cross-sectional widths ranging in size from 3 μm to 70 μm along its length; and
wherein said one or more cross-sectional widths is oriented along the longitudinal axis of said unbranched microchannel and comprises two or more expanded regions separated by a spacer, or two or more expanded regions separated by a spacer and a gradual taper having an initial width greater than a final width and a taper length ranging from 5 to 100 μm.

4. The device of claim 3, further comprising
an inlet channel in communication with said one or more inlet ports and said one or more inlet microchannels; and
an outlet channel in communication with said one or more outlet ports and said one or more inlet microchannels.

5. The device of claim 3, wherein said one or more inlet microchannels is a primary inlet microchannel in communication with one or more microchannel junctions to bifurcate said primary inlet microchannel into two or more secondary inlet microchannels.

6. The device of claim 4, wherein the cross-sectional width of said primary inlet microchannel is greater than at least one of said two or more secondary inlet microchannels.

7. The device of claim 4, wherein said secondary inlet microchannel is in communication with one or more microchannel junctions to bifurcate said secondary inlet microchannel into two or more tertiary inlet microchannels.

8. The device of claim 7, wherein the cross-sectional width of said secondary microchannel is greater than at least one of said two or more tertiary inlet microchannels.

9. The device of claim 7, wherein one or more of said tertiary inlet microchannels is in communication with one or more microchannel junctions to bifurcate said tertiary inlet microchannel into two or more quaternary inlet microchannels.

10. The device of claim 9, wherein the cross-sectional width of said tertiary microchannel is greater than at least one of said two or more quaternary inlet microchannels.

11. The device of claim 9, wherein two or more microchannels selected from the group consisting of a primary inlet microchannel, a secondary inlet microchannel, a tertiary inlet microchannel, and a quaternary inlet microchannel are in communication with a junction that converges to form at least one primary outlet microchannel.

12. The device of claim 11, wherein the cross-sectional width of said primary outlet microchannel is greater than the cross-sectional width of at least one converged microchannel selected from the group consisting of a primary inlet microchannel, a secondary inlet microchannel, a tertiary inlet microchannel, and a quaternary inlet microchannel.

13. The device of claim 11, wherein two or more microchannels selected from the group consisting of a primary inlet microchannel, a secondary inlet microchannel, a tertiary inlet microchannel, a quaternary inlet microchannel, and a primary outlet microchannel in communication with a junction that converges to form at least one secondary outlet microchannel.

14. The device of claim 13, wherein the cross-sectional width of said secondary outlet channel is greater than the cross-sectional width of at least one converged microchannel selected from the group consisting of a primary inlet microchannel, a secondary inlet microchannel, a tertiary inlet microchannel, a quaternary inlet microchannel, and a primary outlet microchannel.

15. The device of claim 13, wherein two or more microchannels selected from the group consisting of a primary inlet microchannel, a secondary inlet microchannel, a tertiary inlet microchannel, a quaternary inlet microchannel, a primary outlet microchannel, and a secondary outlet microchannel in communication with a junction that converges to form at least one tertiary outlet microchannel.

16. The device of claim 15, wherein the cross-sectional width of said tertiary outlet microchannel is greater than the cross-sectional width of at least one converged microchannel selected from the group consisting of a primary inlet microchannel, a secondary inlet microchannel, a tertiary inlet microchannel, a quaternary inlet microchannel, a primary outlet microchannel, and a secondary outlet microchannel.

17. The device of claim 15, wherein two or more microchannels selected from the group consisting of primary inlet microchannel, secondary inlet microchannel, tertiary inlet microchannel, quaternary inlet microchannel, primary outlet microchannel, secondary outlet microchannel, and tertiary outlet microchannel in communication with a junction that converges to form at least one quaternary outlet microchannel.

18. The device of claim 17, wherein the cross-sectional width of said quaternary outlet microchannel is greater than the cross-sectional width of at least one converged microchannel selected from the group consisting of a primary inlet microchannel, a secondary inlet microchannel, a tertiary inlet microchannel, a quaternary inlet microchannel, a primary outlet microchannel, a secondary outlet microchannel, and a tertiary outlet microchannel.

19. The device of claim 3, wherein said inlet microchannel is in communication with one or more junctions that bifurcate said inlet microchannel into two or more division microchannels having a smaller cross-sectional width than said inlet microchannel.

20. The device of claim 19, wherein said division microchannels are in communication with one or more junctions that converge said division microchannels into an outlet microchannel having a greater cross-sectional width than said division microchannel.

21. The device of claim 3, wherein said substrate is selected from the group consisting of glasses, crystals, silicon wafers, plastics, thermoplastics, waxes, gels, hydrogels, polymers, metals, ceramics, organic materials, inorganic materials, and any combinations thereof.

22. The device of claim 3, wherein said microchannels are in communication with one or more junctions that converge on a common outlet microchannel.

23. A method of measuring red blood cell (RBC) deformability comprising:
   a. obtaining a blood sample from a unit of blood or a unit of stored blood;
   b. applying said blood sample to a capillary network device (CND), wherein said capillary network comprises at least one unbranched microchannel of a variable cross-sectional width ranging in size from 3 μm to 70 μm along its length; at least one inlet port in communication with said capillary network microchannel for sample entry; and at least one outlet port in communication with said capillary network microchannel for sample exit; and wherein said variable cross-sectional width is oriented along the longitudinal axis of said unbranched microchannel and comprises two or more expanded regions separated by a spacer, or two or more expanded regions separated by a spacer and a gradual taper having an initial width greater than a final width; wherein said gradual taper has a taper length ranging from 5 to 100 μm; and
   c. measuring RBC deformability in said blood sample and comparing said RBC deformability to a predetermined value; and d. selecting said unit of blood for extended storage or selecting said unit of stored blood for transfusion into a patient in need of a unit of blood.

24. The method of claim 23, wherein said measure of RBC deformability is selected from the group consisting of the flow rate through a CND measured at an inlet port or an outlet port, the number of plugging events of individual microchannels in a CND, the plugging frequency of individual microchannels in a CND, the overall flow rate through the CND and the flow rates in individual microchannels of CND, an aggregate perfusion index comprising the overall flow rate through the CND and the flow rates in individual microchannels of CND, the overall RBC flux through a CND, the RBC flux through individual microchannels of a CND, and the aggregate index comprising the RBC flux measured in various channels of a CND.

25. The method of claim 23, wherein said CND comprises at least one unbranched microchannel of a variable size along its length; at least one inlet to the capillary network microchannel for sample entry; and at least one outlet port from the capillary network microchannel for sample exit.

26. The device of claim 1, wherein said at least one unbranched microchannel further comprises a constant depth ranging from 1 μm to 25 μm.

27. The device of claim 1, wherein said at least one unbranched microchannel further comprises said two or more expanded regions comprising a length ranging from 5 μm to 20 μm.

28. The device of claim 1, wherein said spacer has a width of 5 μm and a length of 16 μm.

29. The method of claim 23, wherein said capillary network comprises a constant depth ranging from 1 μm to 25 μm.

30. The device of claim 1, wherein said gradual taper comprises said initial width of about 8 μm and said final width of about 3 μm.

* * * * *